(12) United States Patent
Sones et al.

(10) Patent No.: US 10,794,905 B2
(45) Date of Patent: Oct. 6, 2020

(54) FLUID FLOW DEVICE ON A POROUS SUBSTRATE AND METHOD FOR MAKING THE SAME

(71) Applicant: University of Southampton, Hampshire (GB)

(72) Inventors: Collin Lawrence Sones, Southampton (GB); Robert William Eason, Southampton (GB)

(73) Assignee: University of Southampton, Southampton, Hampshire (GB)

( * ) Notice: Subject to any disclaimer, the term of this patent is extended or adjusted under 35 U.S.C. 154(b) by 199 days.

(21) Appl. No.: 15/572,190

(22) PCT Filed: May 3, 2016

(86) PCT No.: PCT/GB2016/051267
§ 371 (c)(1),
(2) Date: Nov. 7, 2017

(87) PCT Pub. No.: WO2016/178013
PCT Pub. Date: Nov. 10, 2016

(65) Prior Publication Data
US 2018/0120312 A1    May 3, 2018

(30) Foreign Application Priority Data
May 7, 2015 (GB) .................................. 1507792.8

(51) Int. Cl.
*G01N 33/558* (2006.01)
*B01L 3/00* (2006.01)
(Continued)

(52) U.S. Cl.
CPC ...... *G01N 33/558* (2013.01); *B01L 3/502707* (2013.01); *C12Q 1/48* (2013.01);
(Continued)

(58) Field of Classification Search
CPC ............ B01L 3/502707; B01L 3/5023; B01L 3/502746; B01L 2200/12;
(Continued)

(56) References Cited

U.S. PATENT DOCUMENTS

2009/0298191 A1    12/2009    Whitesides et al.

FOREIGN PATENT DOCUMENTS

| GB | 2527779 A | 1/2016 |
|---|---|---|
| WO | 2008/049083 A2 | 4/2008 |

(Continued)

OTHER PUBLICATIONS

International Search Report and Written Opinion for corresponding Patent Application No. PCT/GB2016/051267 dated Aug. 10, 2016.
(Continued)

*Primary Examiner* — Samuel P Siefke
(74) *Attorney, Agent, or Firm* — Renner, Otto, Boisselle & Sklar, LLP

(57) ABSTRACT

A method of making a fluid flow device comprises providing a substrate of porous material, depositing a radiation-sensitive substance onto the substrate in a pattern defining one or more regions intended to receive and contain fluid during use of the device or occupying an area within such a region, such that the radiation-sensitive substance extends at least partly through the thickness of the substrate below the pattern, and exposing radiation onto the substrate thereby delivering energy to the radiation-sensitive substance in at least part of the pattern to change the radiation-sensitive substance from a first state to a second state through at least part of the thickness of the substrate. One of the first state and the second state may be less permeable than the other.

38 Claims, 8 Drawing Sheets

(51) Int. Cl.
    *C12Q 1/48*      (2006.01)
    *G01N 21/77*      (2006.01)
    *G01N 33/52*      (2006.01)
    *G01N 33/543*      (2006.01)

(52) U.S. Cl.
    CPC .......... *G01N 21/77* (2013.01); *G01N 33/523* (2013.01); *G01N 33/526* (2013.01); *G01N 33/54386* (2013.01); *B01L 2300/126* (2013.01)

(58) Field of Classification Search
    CPC ....... B01L 2300/0848; B01L 2300/126; B01L 2400/086; D21H 25/06; D21H 25/04; G01N 33/558; G01N 21/77; G01N 33/523; G01N 33/526; G01N 33/54386; C12Q 1/48
    See application file for complete search history.

(56) References Cited

FOREIGN PATENT DOCUMENTS

| WO | 2010/003188 | A1 | 1/2010 |
|---|---|---|---|
| WO | 2010/022324 | A2 | 2/2010 |
| WO | 2012/125781 | A2 | 9/2012 |
| WO | 2012/160857 | A1 | 11/2012 |

OTHER PUBLICATIONS

Search Report for corresponding United Kingdom Patent Application No. 1507792.8 dated Oct. 29, 2015.
C. Sones et al.; "Laser-induced photo-polymerisation for creation of paper-based fluidic devices", Lab on a Chip 2014, Issue 14, Sep. 29, 2014, pp. 4567-4575.
Apilux et al.; "Development of automated paper-based devices for sequential multistep sandwich enzyme-linked immunosorbent assays using inkjet printing", Lab on a Chip 2012, Nov. 2012, pp. 126-135.
Akram et al.; "Paper-based microfluidic point-of-care diagnostic devices", Lab on a Chip, May 2013, pp. 2210-2251.
Martinez et al.; "Patterned Paper as a Platform for Inexpensive, Low Volume, Portable Bioassays", Department of Chemistry and Chemical Biology, Harvard University, Angewandte Chemie International Edition, Feb. 2007, pp. 15-19.
Lutz et al.; "Dissolvable fluidic time delays for programming multi-step assays in instrument-free paper diagnositcs", Lab on a Chip, Jul. 21, 2013, pp. 2840-2847.
Bruzewicz et al.; "Low-Cost Printing of Poly(dimethylsiloxane) Barriers to Define Microchannels in Paper", Anal. Chem. 2008, 80, pp. 3387-3392.
Carrilho et al.; "Understanding Wax Printing: A Simple Micropatterning Process for Paper-Based Microlfuidics", Anal. Chem. 2009, 81, pp. 7091-7095.
Elain Fu et al.; "Controlled Reagent Transport in Disposable 2D Paper Networks", Lab on a Chip, Apr. 7, 2010, pp. 918-920.
Fenton et al.; "Multiplex Lateral-Flow Test Strips Fabricated by Two-Dimensional Shaping", Applied Materials & Interfaces, 2009, pp. 124-129.
Girish Chitnis et al.; "Laser-treated hydrophobic paper: an inexpensive microfluidic platform", Lab on a Chip, Mar. 2011.
Delaney et al.; "Electrogenerated Chemiluminescence Detection in Paper-Based Microfluidic Sensors", Analytical Chemistry 2011, 83, pp. 1300-1306.
Olkkonen et al.; "Flexographically Printed Fluidic Structures in paper", Analytical Chemistry, vol. 82, No. 24, Dec. 15, 2010, pp. 10246-10250.
Koji Abe et al.; "Inkjet-Printed Microfluidic Multianalyte Chemical Sensing Paper", Analytical Chemistry, 2008, 80, pp. 6928-6934.
Paul Yager et al.; "Microfluidic diagnostic technologies for global public health", Nature, vol. 442, Jul. 27, 2006, pp. 412-418.
Robert Pelton; "Bioactive paper provides a low-cost platform for diagnostics", Analytical Chemistry, Fol. 28, No. 8, 2009, pp. 925-942.
Wijitar Dungchai et al.; "A low-cost, simple, and rapid fabrication method for paper-based microfluidics using wax screen-printing", Analyst, 2011, 136, pp. 77-82.
Xu Li et al.; "A perspective on paper-based microfluidics: Current status and future trends", Biomicrofluidics 6, 011301 (2012).
Xu Li et al.; "Fabrication of paper-based microfluidic sensors by printing", Colloids and Surfaces B: Biointerfaces 76 (2010), pp. 564-570.
Xu Li et al.; "Paper-Based Microfluidic Devices by Plasma Treatment", Analytical Chemistry, 2008, 80, pp. 9131-9134.
Yao Lu et al.; "Rapid prototyping of paper-based microfluidics with wax for low-cost, portable bioassay", Electrophoresis 2009, 30, pp. 1497-1500.

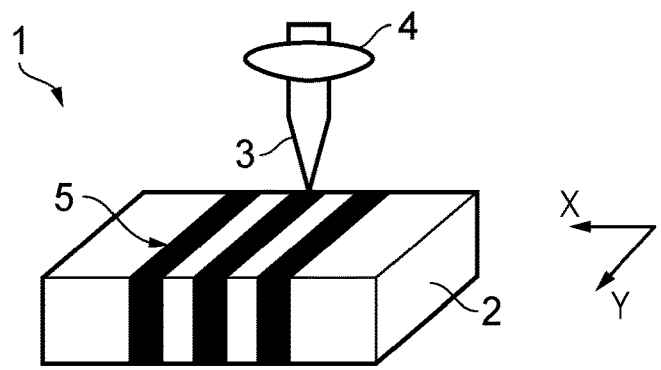
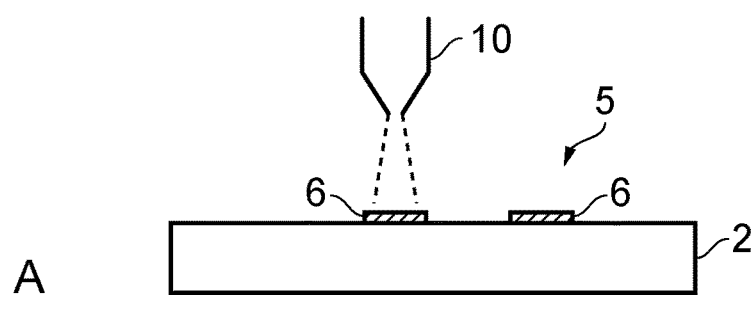
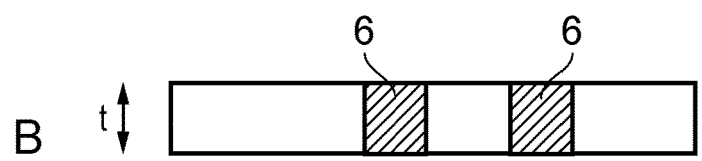
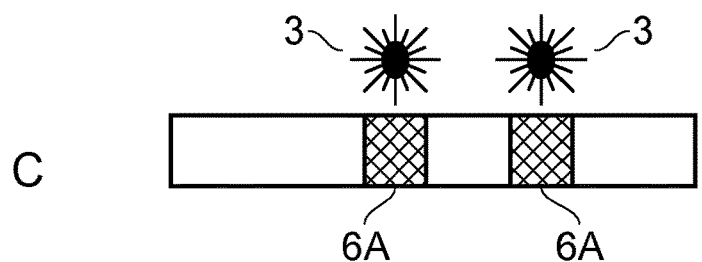
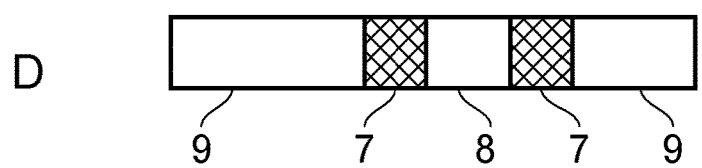
FIG. 2

FLUID FLOW DEVICE ON A POROUS SUBSTRATE AND METHOD FOR MAKING THE SAME

This application is a national phase of International Application No. PCT/GB2016/051267 filed May 3, 2016 and published in the English language, which claims priority to United Kingdom Patent Application No. GB 1507792.8 filed May 7, 2015 which are hereby incorporated herein by reference.

BACKGROUND OF THE INVENTION

The present invention relates to fluid flow devices formed on porous substrates, and methods of making such devices.

Devices configured to deliver a fluid sample from a first location on the device to a second location, for example a test location provided with a reagent, are well-known. One example of an application of such devices is in medical diagnostics, where a sample is deposited on the device for flow to a test location for reaction with a reagent that tests for a disease or other clinical condition or parameter. Often the result of the test is indicated by a colour change at the test location. The device takes the form of a substrate that defines at least one fluid flow path or channel between the deposition site and the test site.

These devices are of great interest because the role of diagnostics and point-of-care (POC) testing is highly beneficial for early clinical detection and subsequent intervention. POC testing provides an effective and rapid technique that excludes or minimises delay by providing a prompt exchange of vital information between the clinical care team and the patient, because the testing can be conducted at the point-of-care (which may be the patient's home, their general practitioner's clinic, or a hospital). The testing is facilitated through the use of uncomplicated, user-friendly and portable testing devices, and much effort has been directed towards producing diagnostic test-kits which are smaller, quicker and smarter, and importantly, cost-effective.

It has been recognised that microfluidic-based "lab-on-chip" (LOC) technology has considerable potential for medical diagnostics devices and systems [1]. Advantages of compact LOC devices include the use of smaller reagent volumes, faster reaction times and portability arising from the smaller device dimensions. These devices were originally developed on platform substrates such as silicon and glass using clean-room based fabrication processes adapted from the semiconductor processing industry. Polydimethylsiloxane (PDMS), a low-cost polymer, has also been considered but has various limitations; this has led to a search for other substrate materials, which now include paper, cotton, thermoplastics and photo-curable polymers. In particular, paper is now considered as a highly suitable substrate for the fabrication of LOC-type devices [2,3]. As a substrate material, paper is inexpensive, abundantly available in a range of different engineered forms that exhibit different properties, can be stored and easily transported, and modified in terms of its liquid transport properties. Additionally, paper-based fabrication procedures themselves are relatively cheap. Paper is currently implemented for analytical and clinical chemistry, and tests are routinely performed for the detection of different chemical species. Two commonly known paper-based clinical tests are the pregnancy test and the lateral flow-based urine dipsticks that can simultaneously detect blood sugar, pH and ketone [4]. Clinical tests that can yield quantitative information of a multiplexed nature (i.e. can perform a series of parallel tests) using a single test strip are very attractive, and microfluidic paper-based analytical devices (µPADs) are an ideal platform for this. These paper-based microfluidic devices have one or more flow channels that are designed to guide and transport an analyte fluid from a point of entry on the device to a reaction zone that has been pre-treated with specific reagents. For paper-based devices the channels may be formed within and extend throughout the thickness of the paper. The walls that delineate the individual channels to contain and guide the flow of liquids may be made from impermeable materials integrated into the structure of the paper.

An early design for these microfluidic devices relied on a cleanroom-based lithographic technique of exposure of UV to a UV-sensitive polymer impregnated in a paper substrate through a custom-designed mask; this cross-linked the polymer to form the required pattern of fluid channels [5]. Lithography has also been proposed elsewhere [6,7]. A development aimed at reducing costs arising from the lithographic procedure involved the use of a modified desktop plotter to dispense an ink composed of PDMS [8]. Other approaches include inkjet printer-based etching of paper impregnated with polystyrene [9], plasma-treatment through a metal mask of a paper impregnated with alkyl ketene dimer [10], paper-cutting using a computer-controlled X-Y knife plotter [11], printing of wax [12,13], inkjet-printing [14,15], flexographic printing [16], wax-screen printing [17], and laser-treatment of a paper with a hydrophobic coating [18]. Each of these techniques has its advantages and disadvantages. Lithography and plasma-treatment require expensive patterning masks or equipment and controlled laboratory conditions. The knife-plotting technique requires specialised or custom-modified patterning equipment, and other techniques may include undesirable post-processing procedures. Other issues are the limitation on achievable feature size resulting from lateral spreading of the material used to delineate channels (for example with wax printing), the need for specialised chemicals and inks (for ink-jet printing), and the use of harsh chemical etchants. Also, some of these techniques may harm the quality of the paper so that the paper's porosity or wicking ability is affected.

An alternative technique has been recently proposed by the present inventors [19]. This uses a light-writing technique to form walls or barriers to define fluid flow channels. The substrate, which may be paper, is impregnated with a radiation-sensitive material that is polymerisable when exposed to radiation, which is then selectively hardened (polymerised) by "writing" the required pattern of barriers over the substrate surface with a radiation beam to provide localised energy to set the light-sensitive material. A development step is then needed to remove the remaining non-hardened (un-polymerised) material using a solvent. Any residual light-sensitive material remaining in the channels after developing can interfere with biological reactions, however.

It is often desirable to control the fluid flow in the device so that the analyte flows along different channels at different speeds. Some of the above fabrication techniques are poorly suited to implement channel designs with required flow rate control, and additional manufacturing steps can be needed to modify the channel network. Proposals for achieving flow rate control include using a circuitous or serpentine channel geometry to delay flow, and forming dissolvable barriers in the flow channels, for example made from sugar [20,21,22]. The above-mentioned light-writing technique has been developed further for the formation of partial barriers to flow within the fluid flow channels [23]. With polymerisable substance impregnated in the substrate, a region within a flow channel is exposed to a controlled amount of light that delivers sufficient energy to cause polymerisation through only part of substrate thickness. A range of porous substrate materials are proposed, including paper, and nitrocellulose membranes [24].

SUMMARY OF THE INVENTION

Accordingly, a first aspect of the present invention is directed to a method of making a fluid flow device comprising: providing a substrate of porous material; depositing a radiation-sensitive substance onto the substrate in a pattern defining one or more regions intended to receive, contain, and/or guide fluid during use of the device or occupying an area within such a region, such that the radiation-sensitive substance extends at least partly through the thickness of the substrate below the pattern; and applying radiation onto the substrate thereby delivering energy to the radiation-sensitive substance in at least part of the pattern to change the radiation-sensitive substance from a first state to a second state through at least part of the thickness of the substrate, wherein when in one of the first state and the second state, the radiation-sensitive substance is less permeable to the fluid than when in the other of the first state and the second state.

Hence, a radiation-sensitive substance may be applied locally to a substrate in accordance with a desired pattern, for example a pattern defining barriers and/or walls for fluid containment, flow and confinement (such as a fluidic network). At least a part of that pattern is then changed to a second state by exposure to radiation. This approach allows the resulting fluidic network to be defined at least in part by the pattern of radiation-sensitive substance deposited on the substrate, not just the control of the application of radiation, allowing more precise control of the generation of walls, barriers or other fluid containing structures in the fluid flow device.

In some cases, the pattern of deposition of the radiation-sensitive substance may be such that the substance is applied to at least one portion of the substrate but not deposited on at least one other portion of the substrate. Hence, manufacturing costs can be reduced compared to impregnating the entire substrate in radiation-sensitive substance, since smaller amounts of the radiation-sensitive substance may be required and the amount of excess radiation-sensitive substance, i.e. that hasn't been converted to the second state, can be reduced.

Various substances can be used as the radiation-sensitive substance. In one example, the radiation-sensitive substance may comprise metal particles which can be deposited on the substrate and then exposed to radiation (e.g. a laser, infrared radiation (heat) or an ion beam) to melt the metal, so that molten metal can spread through the porous material to form walls or barriers. The molten metal then solidifies to form a larger mass of metal than the original metal particles, so that the resolidified mass of metal is in a second state which is less permeable than the first state (the particulate state).

Other examples may use a polymerisable material as the radiation-sensitive substance, for which one of the first state and the second state is a more polymerised state (i.e. has a greater degree of polymerisation) than the other. Preferably, the second state has a greater degree of polymerisation than the first state. A large number of substances are polymerisable; examples of suitable materials are described herein.

In one embodiment, the radiation-sensitive substance may comprise a photoresist, as defined and exemplified below.

In some examples, in the second state, the radiation-sensitive material may be less permeable to the fluid than in the first state, such that when radiation is applied, the radiation-sensitive material becomes less permeable. For example, a negative photoresist may be used. With this approach, the radiation-sensitive substance can be deposited in a pattern corresponding to the positions of desired walls or barriers for delineating the regions of the fluid flow device. When radiation is applied, the substance then becomes less permeable so as to provide structures for containing the fluid. In some cases, all of the radiation-sensitive material may be converted to the second state, in which case there may not be a need for applying solvent to remove excess radiation-sensitive material. In other cases, there may still be some radiation-sensitive material in the more permeable state, but less radiation-sensitive material is wasted compared to the approach of impregnating the entire substrate in radiation-sensitive material.

In other examples, a type of radiation-sensitive substance may be used for which the second state is more permeable to fluid than the first state. One example of such a substance may be a positive photoresist, for which the parts of the substance exposed to radiation may become more permeable and more soluble to solvent, so that applying solvent in a subsequent developing step can remove the parts to which radiation has been applied and leave the remaining parts of the radiation-sensitive substance that are still in a less permeable state to form the walls or barriers or other structures for containing or guiding fluid. Another example may be the metal particles as discussed above.

In some examples, in the less permeable state of the first state and second state, the radiation-sensitive substance may be impermeable to the fluid, so that structures formed from the radiation-sensitive substance in this state may contain fluid or block the flow of fluid.

In other examples, in the less permeable state of the first state and the second state, the radiation-sensitive substance may still be partially permeable, but less permeable than in the other state. Structures formed in this state may be useful for slowing down the flow of fluid compared to the rate of flow through the porous substrate itself.

In some examples, for at least part of the substrate, the radiation-sensitive substance may be deposited to extend through the thickness of the substrate below the pattern on the surface of the substrate, and may then be changed to the second state through the thickness of the substrate. In this way, impermeable walls or partially permeable barriers extending right through the substrate thickness can be created.

In some examples, for at least part of the substrate, the radiation-sensitive substance may be deposited to extend through substantially the entire thickness of the substrate, and the radiation-sensitive substance may be changed to the second state through part of the thickness of the substrate. Alternatively, the radiation-sensitive substance may be deposited so that it extends through just part of the thickness of the substrate, and the radiation-sensitive substance may be changed to the second state through that part of the thickness of the substrate. Both these techniques can be useful for forming barriers which extend through just part of the thickness of the substrate. These barriers can be useful for example for providing structures which act as a filter for filtering certain components from the fluid when the fluid flow device is in use. For example, for a fluid flow device designed for use with blood as the fluid, filtering structures could be provided for blocking red blood cells or other components of the blood while allowing plasma, for example, to pass the filtering structures. The barriers, because of their ability to delay fluids, can be used to separate different constituents of a fluid since each of the individual constituents would be delayed differently. This could in effect be useful for filtering-like applications which are much desired for example in the sample preparation stage of a diagnostic device.

Any combination of such walls and barriers may be generated through the method described above. Thus, a single procedure according to the method can create a device with both fully impermeable walls and barriers providing partial permeability.

Also, in some cases the method may be applied to a substrate which already has some structures or a fluid flow network formed in it, with the method then adding additional walls or barriers or other structures to the substrate.

In some examples, radiation may be applied to the entire substrate surface. Since the pattern of deposition of the radiation-sensitive substance can be varied to control the formation of structures in the fluid flow device, there may be less need to precisely control exposure of certain parts of the substrate to radiation while preventing exposure of other parts of the substrate, which can make the control of the exposing step less complex. For example, the substrate can simply be placed under a lamp or other source of radiation.

On the other hand, for more precise control of the formation of structures in the fluid flow device, other examples may apply radiation to at least one selected part of the substrate, while preventing exposure of at least one other part of the substrate to radiation. In some examples, this could be through the use of a mask for blocking the exposure of certain areas of the substrate to radiation.

In other examples, localised application of radiation can be provided by exposing a beam of radiation onto the substrate, and causing relative translation between the substrate and the beam of radiation. The relative translation may be caused by moving either the substrate or the beam of radiation, or both. In this way, the beam of radiation may move over parts of the deposited pattern of radiation-sensitive material to selectively convert those parts of the material to the second state.

In some examples, the pattern of radiation-sensitive substance deposited may comprise lines defining the regions for receiving, containing or guiding fluid, and during the step of application of radiation (exposure), the relative translation between the substrate and the beam of radiation may be such that the beam of radiation moves over or along the lines of the pattern.

In some embodiments, the beam of radiation has a width in a direction parallel to a width of the lines which is at least equal to the width of the lines, and the exposing comprises aligning the beam of radiation with the lines to expose all of the width of the lines.

In another embodiment the application of radiation comprises aligning the beam of radiation with the lines such that the beam of radiation overlaps an edge of at least one line during the relative translation. The beam of radiation may have a width in a direction parallel to a width of the lines which is equal to or less than the width of the at least one line such than the beam of radiation overlaps only one edge of the at least one line. The beam of radiation may overlap an edge which is adjacent to a region intended to receive and contain fluid during use of the device.

In an alternative embodiment the pattern includes at least one pair of spaced-apart lines, the beam of radiation has a width greater than a width of a space between the pair of spaced-apart lines, and the application of radiation comprises aligning the beam of radiation with the pair of spaced-apart lines to simultaneously expose at least part of the width of both lines in the pair of spaced-apart lines. A flow channel defined by a pair of lines can thereby be created using a single traverse of the radiation beam, rather than one traverse for each line in the pair. Fabrication time may hence be reduced, and the required relative translation simplified. In some cases, a single traverse of the beam could expose more than two lines in a similar way.

The pattern may include at least one pair of spaced-apart lines that define a region in the form of a channel for fluid flow. Alternatively or additionally, the pattern may include lines defining one or more reservoir regions intended to confine received fluid. The pattern might therefore define a fluidic network, comprising any combination of connected or separate channels and reservoirs. The method can therefore be used to produce a fluid flow device of any configuration; the invention is not limited in any way with regard to the shape of the pattern of lines deposited onto the substrate.

Depositing the radiation-sensitive substance may comprise delivering the radiation-sensitive substance onto the substrate using an ink-jet printer. Printing the radiation-sensitive substance in this way enables the formation of highly detailed and also narrow features within the substrate. In some cases, depending on the type of substrate, features as narrow as the fibre structure or pore size of the porous substrate may be formed. It has been shown that barrier or wall with widths of approximately 100 μm can be formed using paper as the substrate. However, it is expected that features of dimensions of 50 μm or smaller may be formed.

The application of radiation may commence before the depositing is complete. This can facilitate alignment between the deposited pattern and the radiation beam, and also may increase fabrication speed. For example, the depositing and the application of radiation may be performed using an inkjet printer head and a radiation beam delivery system which are carried on a common assembly, the relative translation being between the substrate and the common assembly.

Alternatively, depositing the radiation-sensitive substance may comprise spray printing, or a lithographic technique, although other depositing techniques may also be used.

The beam of radiation may be a beam of laser light. Radiation sources other than lasers are not precluded, however.

The radiation-sensitive substance may be a polymerisable substance or a photoresist, for example.

Examples of suitable porous materials for the substrate include paper and nitrocellulose. Other examples may include sintered materials such as sintered glass.

The method may further comprise depositing a biological or chemical reagent onto one or more regions on the substrate. In some embodiments, the method comprises depositing the reagent before the exposing.

A second aspect of the invention is directed to a fluid flow device fabricated using the method of the first aspect.

A third aspect of the invention is directed to an apparatus configured to make a fluid flow device in accordance with the method of the first aspect.

BRIEF DESCRIPTION OF THE DRAWINGS

For a better understanding of the invention and to show how the same may be carried into effect reference is now made by way of example to the accompanying drawings in which:

FIG. 1 shows a simplified schematic perspective view of a system for performing part of a method according to embodiments of the invention;

FIG. 2 shows a schematic illustration of steps in a method according to an embodiment of the invention;

DETAILED DESCRIPTION

Definitions

Figure 3:
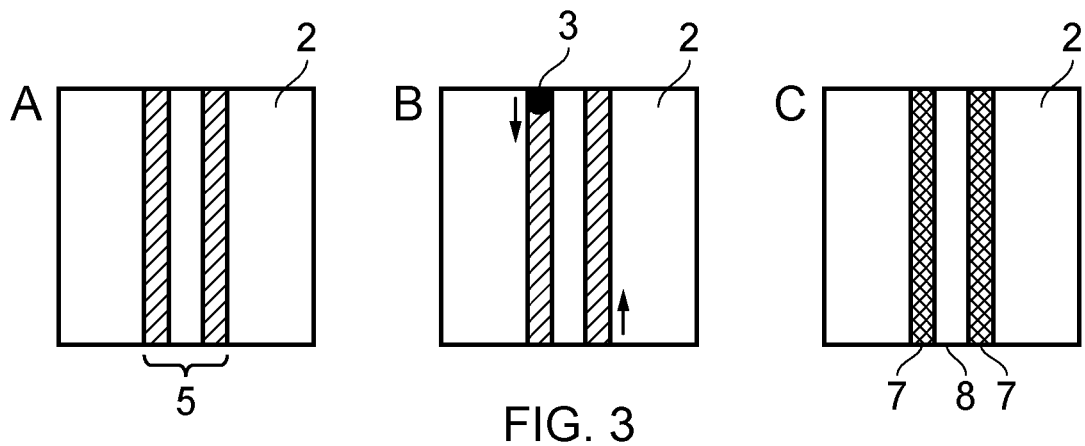
FIGS. 3, 4, 5 and 6 show plan views of a substrate at various stages in methods according to embodiments of the invention, each embodiment employing a different light beam spot size and alignment.

"Radiation" herein refers to any form of radiative energy, including energy transferred by waves or particles. Examples include electromagnetic radiation (including any part of the electromagnetic spectrum, e.g. radiofrequency radiation, microwaves, visible light, infrared radiation, ultraviolet radiation, X-ray radiation, gamma radiation etc.); radiation of particles (e.g. electron beam, ion beam, etc), or acoustic radiation (e.g. ultrasound).

"Radiation-sensitive substance" refers to any substance or combination of multiple substances which, when radiation is applied thereto, changes from a first state to a second state, where the substance is less permeable in one of the first state and the second state than the other. In some embodiments, the radiation-sensitive substance comprises one or more polymerisable substances, as described herein.

"Wall" refers to a structure of the fluid flow device that extends substantially through (e.g. completely through) the thickness of the substrate and is impermeable to the fluid for which the device is intended to be used.

"Barrier" refers to a structure of the fluid flow device which is less permeable than other parts of the substrate, but which is not completely impermeable to the fluid for which the device is intended to be used. The barrier may be partially permeable because the barrier does not extend through the entire thickness of the substrate, or because the substance forming the barrier is partially permeable, or both.

"The depositing" refers to the depositing of the radiation-sensitive substance on the substrate.

"The application of radiation" refers to the application of radiation to at least part of the substrate, such that at least part of the substrate is exposed to radiation.

The following description describes a technique suitable for defining fluid-containing regions such as flow channels, wells and reservoirs in a substrate or membrane made from porous material, such as paper, nitrocellulose or sintered glass. The regions are defined by barriers or walls within the substrate at the boundaries of each region, such as at each side of a channel. The walls are formed from a less permeable state of a radiation-sensitive substance, for which conversion between a more permeable state and the less permeable state is induced by exposure to radiation energy.

Various techniques may be used to form the structures, but in one example a pattern of lines of the radiation-sensitive substance corresponding to the desired locations of the barriers or walls is deposited onto the substrate and allowed to permeate through the substrate thickness, and then a beam of radiation, such as a laser beam, is used to "write" over the pattern so that the energy delivered by the radiation changes the state of the radiation-sensitive substance beneath the beam to the less permeable state. The less permeable state may be wholly impermeable to fluid to form walls for confining fluid to channels, wells or reservoirs, or largely or partially impermeable to fluid to form barriers for slowing down the flow of fluid or providing filtering structures.

Radiation-Sensitive Substances

The method of the present technique uses radiation to create regions of less permeable material (e.g. the walls or barriers of fluid-containing regions) within areas of porous material (e.g. the inside of the channels, reservoirs and similar, plus areas outside the fluid-containing regions) in a porous substrate such as paper or nitrocellulose. To achieve this, a radiation-sensitive substance is used which can be altered or changed from a first state to a second state by the application of radiation. One of the first state and the second state is a less permeable state, in some cases an impermeable state, in which the substance takes the form of a material that does not allow fluid to pass through it and can therefore be used to create a physical wall or barrier to fluid flow within the material of the substrate. The less permeable state may in some examples be hydrophobic, as this helps in containing larger volumes of aqueous fluids within the flow channel structure for longer times. However, radiation-sensitive substances having a less permeable state which is not hydrophobic can also be used, and may provide adequate fluid containment. The other more permeable state is typically a liquid state so that the radiation-sensitive substance can be conveniently applied to the substrate in a pattern corresponding to the desired locations of the walls or barriers. For example, the substance is deposited onto the substrate surface in the required pattern and then permeates or soaks into the substrate below the pattern so that a volume of material extending through the thickness of the substrate becomes impregnated with the radiation sensitive substance.

Any radiation-sensitive substance, compound, chemical or material which behaves in this way and which can be impregnated into the substrate material in the desired pattern can be employed in the present invention. Various techniques may be employed for depositing the substance onto the substrate in the pattern; these are discussed further later.

In some examples, the radiation-sensitive substance is transformed by radiation exposure from a first state to a second, less permeable, state, and hence can be considered to operate in a negative regime. The less permeable state may be a partially permeable state or a fully impermeable state. In some examples, the less permeable state may be a solid state.

In other examples, the radiation-sensitive substance may operate in an opposite, positive regime, in which exposure to radiation transforms the substance from a first state to a second, more permeable state. With this approach, the substance can be laid down in areas of the substrate corresponding to both the walls/barriers and the fluid containing regions within the walls/barriers. Radiation may then be applied locally to the fluid containing regions but not the walls/barriers to selectively convert the fluid containing regions to the more permeable state (e.g. a liquid state). A subsequent development step may then use solvent to remove the radiation-sensitive substance that is in the more permeable state, but not the less permeable walls/barriers.

Use of a negative-type radiation-sensitive substance may often be more convenient (it may require less radiation-sensitive substance to be deposited and less removal of excess radiation-sensitive substance using a solvent or other developer), and for the subsequent description a negative-type substance will be described. However, it will be appreciated that positive-type substances could also be used.

For a negative-type radiation-sensitive substance, exposure of the substance to radiation forms less permeable material within the substrate in the exposed areas. Hence, if the radiation is applied in the form of a beam which is moved to follow lines of the deposited pattern, the substance is hardened along the lines so as to become walls or barriers for fluid-containing regions. The width of the beam can be chosen relative to the width of lines in the pattern to be narrower, the same or wider, and aligned exactly or with an overlap, so as to expose all or only some of the substance. Various effects can thereby be achieved; these are described in more detail later.

Radiation-sensitive substances suitable for use in the invention include materials sometimes referred to as polymerisable substances, photoresists, and radiation-curable resins and adhesives, and other similar materials.

Typically, the polymerisable substance is a substance containing molecules (monomers) which, on the application of radiation, bond to one another to form a polymer. The polymer may be more permeable or less permeable than the polymerisable substances from which it is formed. Typically, the polymer is less permeable than the polymerisable substances from which it is formed. In some examples, the more permeable state may be a liquid state and the less permeable state may be a state which is more solid, firm or hard.

The polymerisable substance may comprise (or consist of) a monomer molecule. In this specification the term "monomer molecule" means a molecule capable of undergoing polymerisation to thereby form the constitutional units of a polymer.

The polymer formed from the monomer molecules is typically an organic polymer. A large number of organic polymers are known in the art. Examples of particular classes of organic polymers suitable for use according to the present invention include polyolefins, polyesters, polycarbonates, polyamides, polyimides, polyether sulfones, and mixtures or derivatives thereof.

In the technique of the present invention, the monomer molecule is typically capable of radiation-initiated polymerisation (i.e. polymerisation initiated by the application of radiation, as defined herein). Examples of such monomer molecules include ethylenically unsaturated monomers. Any compound having a carbon-carbon double bond and which is capable of being polymerised by the application of radiation may function as an ethylenically unsaturated monomer.

In one embodiment, the ethylenically unsaturated monomer may be an olefin: in other words, an unsubstituted, unsaturated hydrocarbon (such as ethylene, propylene, 1-butene, 1-hexene, 4-methyl-1-pentene or styrene). In this specification polymers formed by polymerising such monomers are termed 'polyolefins'.

In another embodiment, the ethylenically unsaturated monomer is an ethylenically unsaturated hydrocarbon substituted with one or more functional groups; examples of such functional groups include the substituents defined and exemplified below in relation to the substituent group $R_2$ on an acrylate or methacrylate group; further examples include halogen atoms, particularly fluorine atoms (examples of olefins substituted with such groups include vinylidene fluoride or tetrafluoroethylene) or chlorine atoms (examples of olefins substituted with such groups include vinyl chloride and vinylidene dichloride), carboxylic acid or carboxylic ester groups (examples of olefins substituted with such groups include acrylic or methacrylic monomers, as described and exemplified below), nitrile groups (examples of olefins substituted with such groups include acrylonitrile and methacrylonitrile). In this specification polymers formed by polymerising such monomers are termed 'substituted polyolefins'.

In one embodiment, the ethylenically unsaturated monomer is a (meth)acrylate monomer. These are monomers of the formula:

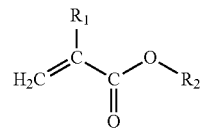

wherein $R_1$ is hydrogen or methyl, and $R_2$ is hydrogen or a substituent, or two groups $R_2$ together form a linker group. When $R_1$ is hydrogen, the monomer is an acrylate monomer. When $R_1$ is methyl, the monomer is a methacrylate monomer.

When $R_2$ is a substituent, the substituent may comprise or consist of a hydrocarbyl group, typical examples of which include alkyl, alkenyl, alkynyl, cycloalkyl, heterocyclyl, aryl and heteroaryl groups. In one embodiment the substituent may comprise or consist of an alkyl group. In this specification the term "alkyl group" means a saturated, monovalent, hydrocarbon moiety. The alkyl group is typically a $C_{1-30}$ alkyl group, such as a $C_{1-10}$ alkyl group, such as a $C_{1-6}$ alkyl group, such as a $C_{1-4}$ alkyl group, such as a methyl, ethyl, n-propyl, isopropyl, n-butyl, isobutyl, sec-butyl, or tert-butyl. The alkyl group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R') where R' is hydrogen or a substituent, typically a $C_{1-6}$ alkyl group or a benzyl group.

In one embodiment the substituent may comprise or consist of an alkenyl group. In this specification the term "alkenyl group" means a monovalent, hydrocarbon moiety having at least one carbon-carbon double bond. The alkenyl group is typically a $C_{2-10}$ alkenyl group, such as a $C_{2-6}$ alkenyl group. The alkenyl group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R') where R' is hydrogen or a substituent, typically a C$_{1-6}$ alkyl group or a benzyl group.

In one embodiment the substituent may comprise or consist of an alkynyl group. In this specification the term "alkynyl group" means a monovalent, hydrocarbon moiety having at least one carbon-carbon triple bond. The alkynyl group is typically a C$_{2-10}$ alkynyl group, such as a C$_{2-6}$ alkynyl group. The alkenyl group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R') where R' is hydrogen or a substituent, typically a C$_{1-6}$ alkyl group or a benzyl group.

In one embodiment the substituent comprises or consists of a cycloalkyl group. In this specification the term "cycloalkyl group" means a monovalent, saturated, cyclic hydrocarbon group. The cycloalkyl group is typically a C$_{3-10}$ cycloalkyl group, such as a C$_{3-8}$ cycloalkyl group, such as a C$_{4-6}$ cycloalkyl group. The cycloalkyl group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group.

In one embodiment the substituent comprises or consists of a heterocyclyl group. In this specification the term "heterocyclyl group" means a monovalent, saturated, cyclic group, having 1 to 4 heteroatoms selected from nitrogen, oxygen and sulphur. The heterocyclyl group is typically a 5- or 6-membered heteroaryl group, such as a tetrahydrofuryl, pyrrolidinyl, tetrahydrothienyl, oxazolidinyl, isoxazolidinyl, thiazolidinyl, isothiazolidinyl, thiadiazolidnyl, piperidinyl, piperazinyl or morpholinyl group. The heterocyclyl group may be substituted with one or more substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group.

In one embodiment the substituent comprises or consists of an aryl group. In this specification the term "aryl group" means a monovalent, unsaturated, aromatic group (ie an unsaturated group having 4n+2 pi electrons, where n is an integer, preferably 1 or 2). The aryl group is typically a C$_{6-10}$ aryl group, such as a phenyl or naphthyl group. The aryl group may be substituted with one or more substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group.

In one embodiment the substituent comprises or consists of a heteroaryl group. In this specification the term "heteroaryl group" means a monovalent, unsaturated, aromatic group, having 1 to 4 heteroatoms selected from nitrogen, oxygen and sulphur. The heteroaryl group is typically a 5- or 6-membered heteroaryl group, such as a furyl, pyrrolyl, thienyl, oxazolyl, isoxazolyl, thiazolyl, isothiazolyl, triazolyl, thiadiazolyl, tetrazolyl, pyridiyl, pyrimidyl, pyrazinyl or triazinyl group. The heteroaryl group may be substituted with one or more substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group.

Examples of acrylate and methacrylate monomers include acrylic acid (R$_1$ and R$_2$ are H) methacrylic acid (R$_1$ is methyl and R$_2$ is H), and acrylic and methacrylic esters such as methyl acrylate (R$_1$ is H and R$_2$ is methyl), ethyl acrylate (R$_1$ is H and R$_2$ is ethyl), 2-ethylhexyl acrylate (R$_1$ is H and R$_2$ is 2-ethylhexyl), hydroxyethyl methacrylate (R$_1$ is H and R$_2$ is 2-hydroxyethyl), butyl acrylate (R$_1$ is H and R$_2$ is butyl) and butyl methacrylate (R$_1$ is methyl and R$_2$ is butyl).

When two groups R$_2$ together form a linker group, the monomer is a diacrylate or dimethacrylate. The linker group may be an aliphatic chain (for example an alkylene group or an oxyalkylene group), an alicyclic linker ring (for example a cycloalkylene, arylene or heteroarylene ring), or a combination thereof.

In one embodiment the linker group comprises or consists of an alkylene group. In this specification the term "alkylene group" when used to define the linker group means an aliphatic, saturated, divalent, hydrocarbon moiety. The alkylene group is typically a C$_{1-30}$ alkylene group, such as a C$_{1-10}$ alkylene group, such as a C$_{1-6}$ alkylene group, such as a C$_{1-4}$ alkylene group, such as a methylene, ethylene, methylmethylene, propylene or butylene group, and especially an ethylene group. The alkylene group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group. In one embodiment, the substituent on the alkylene group links the alkylene group to the rest of the linker group, such as those defined and exemplified below.

In one embodiment the linker group comprises or consists of a cycloalkylene group. In this specification the term "cycloalkylene group" when used to define the linker group means a divalent, saturated hydrocarbon group. The cycloalkylene group is typically a C$_{3-10}$ cycloalkylene group, such as a C$_{3-8}$ cycloalkylene group, such as a C$_{4-6}$ cycloalkylene group. The cycloalkylene group may be substituted with one or more (typically only one) substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group. In one embodiment, the substituent on the cycloalkylene group links the cycloalkylene group to the rest of the linker group, such as those defined and exemplified below.

In one embodiment the linker group comprises or consists of an arylene group. In this specification the term "arylene group" when used to define the linker group means a divalent, unsaturated, aromatic group. The arylene group is typically a C$_{6-10}$ arylene group, such as a phenylene group or naphthylene group. The arylene group may be substituted with one or more substituent, examples of which include halogen (especially fluorine or chlorine), hydroxy, nitrile (—CN), carboxylic acid (—CO$_2$H) and carboxylic ester (—CO$_2$R) where R is hydrogen or a substituent, typically a C$_{1-6}$ alkyl group or a benzyl group. In one embodiment, the substituent on the arylene group links the arylene group to the rest of the linker group, such as those defined and exemplified below.

In another embodiment the linker comprises or consists of an oxyalkylene or polyoxyalkylene group. An oxyalkylene group has the formula:

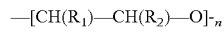

wherein R$_1$ and R$_2$ are hydrogen or a C$_{1-4}$ alkyl group, such as a methyl group, and n is typically 1 to 350, such as 1 to 100, such as 1 to 50, such as 1 to 20, such as 1, 2, 3, 4, 5, 6, 7, 8, 9, or 10. When n is 1, the linker comprises an oxyalkylene group: when n is 2 or more, the linker comprises a polyoxyalkylene group. Typically the linker group is a oxyethylene or polyoxyethylene group (i.e. wherein $R_1$ and $R_2$ are hydrogen).

In another embodiment the linker comprises or consists of an ester (—C(=O)—O—) group. In another embodiment the linker comprises or consists of an amide (—C(=O)-N(R")-) group, where R" is hydrogen or a substituent, typically a $C_{1-6}$ alkyl group or a benzyl group. In another embodiment the linker comprises or consists of an ether (—O—) group. In one embodiment, the linker comprises or consists of a urethane (—O—C(=O)-NR"-) group (where R" is as defined above).

In one embodiment, the linker group comprises both an alkylene group (as defined and exemplified above) and an oxyalkylene or polyoxyalkylene group (as defined above). The linker group may comprise an oxyalkylene or polyoxyalkylene group having two alkylene termini. In this embodiment, the oxyalkylene or polyoxyalkylene group may be bonded directly to the two alkylene termini or may be bonded via a linker group, typically an ester group.

In one embodiment, the linker group comprises both an alkylene group, cycloalkylene group and/or an arylene group (as defined and exemplified above) and one or more urethane groups (as defined above). In one embodiment, the linker group may an alkylene, cycloalkylene group /or an arylene group having two urethane termini. In this embodiment, the alkylene, cycloalkylene group /or an arylene group may be bonded directly to the two urethane termini or may be bonded via a further linker group, such as those defined and exemplified above.

Examples of such diacrylates and dimethacrylates include alkylene diacrylate or dimethacrylates (where two groups $R_2$ together form alkylene, as defined and exemplified above, especially ethylene glycol diacrylate or dimethacrylate) and glycol ether diacrylates and dimethacrylates, such as polyalkylene glycol diacrylates and polyalkylene glycol dimethacrylates, where two groups $R_2$ together form an oxyalkylene or polyoxyalkylene group, as defined and exemplified above) polyethylene glycol dimethacrylate. The polyethylene glycol moiety of polyethylene glycol diacrylates and polyethylene glycol dimethacrylates typically has an average molecular weight ranging from 200 to 20,000, typically 200 to 1000.

Further examples of such diacrylates and dimethacrylates include urethane diacrylates or dimethacrylates (where two groups $R_2$ together form a linker including a urethane linkage, as defined and exemplified above). A particular example is the urethane di(meth)acrylate sold as OP-66-LS by DYMAX Corporation.

Further examples of acrylates include the acrylate monomer sold as ABELUX A4061T by DYMAX Corporation.

In another embodiment, the monomer is a mercapto ester. As is known to the person skilled in the art, mercapto esters have the formula R-C(=O)-SR' wherein R and R' are substituents, as defined above in relation to the substituents $R_2$ on an acrylate or methacrylate group, especially, alkyl, aryl or heteroaryl groups. These may be copolymerised with a number of other co-monomers, such as triallyl isocyanurate (CAS No. 1025-15-6) or tetrahydro-2-furanylmethyl methacrylate. Examples of co-monomer mixtures include those sold as Norland 61 and Norland 68 by Norland Products Incorporated.

The polymer formed from the monomers may be cross-linked. Typically, a cross-link is a region in the polymer from which at least four chains emanate, and is typically formed by reactions involving sites or groups on the existing polymer structure or by interactions between existing polymers. The region may be a direct bond between the polymer chains, a single atom (such as an oxygen or sulphur atom), a group of atoms (such as an alkylene group or alkyleneoxy group, as defined and exemplified above), or a number of branch points connected by bonds, groups of atoms, or oligomeric chains. Cross-linking of the polymer chains can result in a network polymer. The degree of cross-linking of a network polymer may vary depending on the nature of the polymer and the conditions and reagents used to produce it. Examples of suitable reagents and conditions are well known to those skilled in the art. The degree of cross-linking can influence the mechanical strength of the polymer and the degree of permeability to a fluid.

The polymerisable substance may be polymerised by any method known to those skilled in the art. Examples of polymerisation methods include radical polymerisation (in which the reactive species which carry the polymerisation chain reaction are free radicals), cationic polymerisation (in which the reactive species which carry the polymerisation chain reaction are cations), anionic polymerisation (in which the reactive species which carry the polymerisation chain reaction are anions), or any combination thereof. It is preferred that the polymerisation method is radical polymerisation, as this mechanism is most easily induced by radiation.

In one embodiment, the monomer is polymerised in the presence of a photoinitiator. A photoinitiator is a chemical compound that decomposes into free radicals when radiation is applied. The photoinitiator may be a Type I or Type II photoinitiator. Type I photoinitiators undergo cleavage upon irradiation to generate two free radicals in which only one is reactive and proceeds to initiate polymerization. Type II photoinitiators form an excited state (e.g. a triplet state) upon irradiation but must abstract an atom or electron from a donor synergist, which then acts as the initiator for polymerization.

Examples of photoinitiators are well known to those skilled in the art. Examples of Type I photoinitiators include azobis(isobutyronitrile) (AIBN), peroxides such as benzoyl peroxide, benzoin ethers, benzil ketals, a-dialkoxyacetophenones, α-aminoalkylphenones, α-hydroxyacetophenones, and acyl phosphine oxides. Examples of Type II photoinitiators include diaryl ketones (benzophenones) such as benzophenone and substituted benzophenones, thioxanthones such as isopropyl thioxanthone and 2,4-diethylthioxanthone, and quinones such as benzoquinone, camphorquinone and anthraquinone.

In one embodiment, the radiation sensitive material comprises (or consists of) a photoresist. Photoresists are classified into two groups: positive resists and negative resists. In the context of the present technique, the term "positive resist" means a type of photoresist in which the portion of the photoresist that is exposed to radiation becomes more permeable to the fluid intended to be received, contained, and/or guided during use of the device. The portion of the positive photoresist that is unexposed remains less permeable to the fluid. In contrast, in the context of the present technique, the term "negative resist" means a type of photoresist in which the portion of the photoresist that is exposed to radiation becomes less permeable to the fluid intended to be received, contained, and/or guided during use of the device. The unexposed portion of the negative photoresist remains more permeable to the fluid. In one embodiment, the photoresist is a negative photoresist.

The invention is not limited to any particular radiation-sensitive substance. Radiation-sensitive or photosensitive materials other than those described above but which nevertheless behave in a similar manner may be used to implement the various embodiments of the invention. The type of radiation (e.g. wavelength of electromagnetic radiation) and the level of energy density needed will depend on the choice of radiation-sensitive substance and the thickness and structure of the substrate. Various radiation-sensitive substances may require more than one form of radiation exposure, e.g. a heat treatment after a light exposure stage to harden or produce the required properties; methods according to various embodiments of the invention may include such a step if necessary.

As examples of radiation-sensitive substances, the inventors have used the polymerisable substances DeSolite (registered trade mark) 3471-3-14 (from DSM Desotech Inc. or Chemtrec International, USA), in which the monomer is a glycol ether acrylate, and SUBSTANCE G (from Maker-Juice, USA), in which the monomer is an acrylate ester, to implement embodiments of the invention. As mentioned, however, other radiation-sensitive substances with the appropriate characteristics could be used.

In some examples, two or more different types of radiation-sensitive substances may be deposited on the substrate. For example, a first type of radiation-sensitive substance may be deposited in a first pattern and a second type of radiation-sensitive substance may be deposited in a second pattern. The different types of radiation-sensitive substance may have different properties, e.g. different permeability when in the less permeable state, different energy density (energy per unit area) of radiation required for converting the state of the substance, etc. This can allow for further control of the generation of substances in the fluid flow network, e.g. with a single source of radiation having a set energy density, structures of differing permeability can be created using the two or more different types of radiation-sensitive substance.

Fluid Flow Channel Formation

Information regarding a light-writing technique used to create fluid flow channels by creating walls extending through the full thickness of a paper substrate has been previously presented [19]. In this technique, the substrate is completely impregnated with a light-sensitive substance by soaking the substrate in the substance, and a light beam is moved over the substrate to selectively harden the substance in exposed areas only. After exposure, the substrate is subjected to a development stage in which a solvent is used to remove non-hardened light-sensitive substance which has not been exposed to the light. Hence, it is the relative motion between the light beam and the substrate which defines the pattern of solid material and hence the channel structure.

In contrast, with the technique described herein the radiation-sensitive substance is deposited in desired patterns, e.g. patterns of walls or barriers, and then radiation is then applied to the substrate; in one embodiment, the substrate may be exposed in general to radiation; in another embodiment, a radiation beam may follow the same pattern. Hence, the pattern of walls and barriers is defined at least in part by the deposition of the substance, rather than the application of radiation. One advantage is that areas of the substrate which are not deposited with the substance retain the inherent properties of the substrate, such as the porosity or natural wicking ability of the substrate. Also, less radiation-sensitive substance is needed, and there is less excess substance to be removed in a development stage. In some examples, the development stage may be eliminated entirely since all the radiation-sensitive substance can be converted to a less permeable state, which is both more efficient, and avoids problems associated with residual radiation-sensitive substance remaining in the substrate. In other examples, there may still be some excess radiation-sensitive substance in the more permeable state, for instance following deposition the radiation-sensitive substance may have spread outwards while soaking through the substrate, so that there is some substance beyond the location of the deposited surface pattern, and depending on the width and positioning of the beam of radiation used this may lead to some parts of the substance not being converted into the less permeable state, in which case some development may still be required. Nevertheless, the amount of excess radiation-sensitive substance to be removed can be greatly reduced.

According to some embodiments, inscription of a desired pattern of fluid flow channels in a porous substrate is achieved via a laser-based direct-write procedure that is based on the principle of radiation-induced polymerisable substanceisation. As with known laser direct-write procedures for other applications, the method uses scanning of a light beam from a laser (or other light source) across the surface of the work-piece or substrate, which in some embodiments is paper. This relative translational movement of the light beam and the substrate can be achieved by movement of the light beam across a stationary substrate, movement of the substrate with respect to a stationary light beam, or a combination of the two. Computer control of scanning stages holding the substrate or the laser, and/or mirrors and lenses to direct the light beam, can be used to automatically and precisely define the pattern of writing, in a repeatable yet easily modifiable way. Similar techniques may be used for other types of radiation. Mass production, prototype manufacture and small production runs can be readily achieved with the same apparatus. Deposition of the pattern of radiation-sensitive substance can also be conveniently achieved via several readily repeatable techniques, such as deposition using an inkjet printer head, stylus, liquid dropper, etc.

FIGS. 1 to 7 describe embodiments of the invention that use a laser as the source of radiation energy; other radiation sources may be used. FIG. 1 shows a highly simplified schematic representation of a system 1 for performing the light exposure stage, using a laser, in methods according to embodiments of the invention. A planar substrate 2 of, for example, paper has had deposited on it a pattern 5 of radiation-sensitive substance arranged in three parallel lines. The substance has penetrated through the thickness of the substrate. The radiation-sensitive substance may be a polymerisable substance, examples of which are described above. A laser (not shown) delivers a light beam 3 which is directed and focussed onto the surface of the substrate 2 using one or more mirrors or lenses 4. Note that an unfocussed light beam might alternatively be used. Relative translation in the X and Y directions (in the plane of the substrate) between the substrate surface and the light beam is used to trace the light beam 3 along the pattern 5 of lines on the surface of the substrate 2. The light delivers energy into the substrate below the exposed parts and hence into the deposited polymerisable substance to polymerise the substance, thereby creating a series of less permeable polymer lines (walls or barriers) within the substrate. In this example, a set of three parallel walls is created. Each pair of adjacent walls can form a fluid flow channel, so in this example two parallel channels having a shared wall or barrier are created.

FIG. 2 shows a schematic illustration of stages in an embodiment of the invention, as side views of the substrate.

In stage A (deposition), the porous substrate 2 has applied to it a pattern 5 of radiation-sensitive substance 6 in the form of a curable polymerisable substance (e.g. resist, resin or adhesive). In this example, the pattern 5 is a pair of spaced-apart lines. The polymerisable substance 6 is deposited by printing it onto the substrate surface using an inkjet printer head 10. In stage B, the polymerisable substance 6 soaks into the substrate 2 to extend through the thickness t of the substrate below the deposited pattern. There may be some horizontal spreading of the substance through the substrate as the substrate soaks down vertically. In stage C (exposure), the light beam 3 is scanned directly over the surface of the substrate 2 along or over the lines of the pattern 5. Under each line, the volume of the substrate containing the polymerisable substance is exposed to a sufficient amount of light energy to cause polymerisation of the polymerisable substance so that it is changed to the impermeable state so that two walls of solid polymer 6A are formed. The walls extend through the thickness t of the substrate 2, from the top surface to the bottom surface. Stage D shows the final substrate, which may be a completed fluid flow device, or may require further manufacturing steps to produce the device. The impermeable polymerisable substance 6A forms two walls 7 which define boundaries for a region of the substrate between the walls 7 which has not received any polymerisable substance and hence comprises plain untreated substrate material, and which is therefore a region 8 for receiving and containing fluid since the walls 7 will act to contain fluid introduced into that region. Depending on the positions of the walls 7, the region 8 might be a flow channel so that received fluid flows along the channel by wicking. Alternatively, the walls 7 might define region having the form of a well or reservoir, which receives and then confines fluid with little or no flow. A well or reservoir might be connected to one or more channels that deliver fluid to and/or from the well or reservoir. The regions 9 on the other, outer, sides of the walls 7 are also plain untreated substrate material.

In other examples, the radiation-sensitive substance 6 may be converted to a less permeable, but still partially permeable state, to form barriers which are not fully impermeable, which can be useful for controlling, e.g. slowing, flow of fluid.

Also, it is possible to control the light beam to partially convert the deposited substance 6 to a less permeable state, to create a partial barrier which extends through less than the full thickness of the substrate. For example, rather than using a continuous wave laser, a pulsed laser can be used with the repetition rate of the laser controlling the energy density applied to the substrate and hence the extent to which the substance 6 is converted to the less permeable state. This can be useful for providing fluid flow control structures for reducing flow rate in the device, or for providing filtering structures for filtering particles of a given size from the fluid.

FIG. 3 shows schematic plan views of a substrate during various stages of an example of a method according to the invention. FIG. 3A shows a substrate which has had a pattern 5 of polymerisable substance deposited onto it by inkjet printing. The pattern comprises a pair of parallel lines, and is simplified for the purposes of illustration. In reality, the pattern will likely comprise a more complex shape of lines to define a network of one or more channels, wells, reservoirs or other regions which may or may not be connected, and may lead between one or more sample deposition sites and one or more reaction sites. For each flow channel, the pattern may comprise a pair of spaced-apart lines, however. The lines in the pair may or may not be parallel; it may be desired to vary the width of the channel along its length to modify fluid flow rate or accommodate a reagent site, for example. FIG. 3B shows the substrate ready for the laser writing stage. A light beam 3 is directed onto the surface of the substrate 2 and aligned with a line of the pattern 5. The light beam 3 will be moved relative to and over the substrate surface so that it follows the path of the line as closely as possible, in the direction indicated by the arrow. The light beam 3 will then be aligned with the second line of the pattern 5, and traced along that also, perhaps in the opposite direction as shown by the arrow, or alternatively by returning the light beam 3 to the start of the pattern and following the direction used for the first line. Note that the beam of light 3 has a width in a direction orthogonal to its direction of travel, and hence parallel to the width of the lines, which is substantially equal to the width of each line. In this example, the full width of the polymer lines is polymerised, and no un-polymerised material is left in the substrate 2, but other examples may still have a small amount of un-polymerised material remaining. To ensure polymerisation of the polymerisable substance through the full thickness of the substrate, a sufficient amount of light energy is delivered by the light beam. This can be controlled by appropriate selection of the power or intensity of the light beam and the speed of the translational movement. For a given level of energy density to be applied, a fast writing speed may require a higher intensity, and a low writing speed can be combined with a lower intensity. A faster speed will decrease production times. On the other hand, different depths/amounts of polymerisation can be provided by controlling one or both of the intensity and the writing speed of the light beam to vary the energy density (energy per unit area of the substrate) applied to the substrate, to allow for precise control of the structures formed. FIG. 3C shows the substrate 2 after the light writing, when the polymer has been polymerised and the walls 7 of hardened material have been formed, bounding a channel 8. As mentioned, the width of the walls 7 is the same as the width of the originally deposited lines 5 since the full line width has been exposed to the light beam 3.

While the method described with respect to FIG. 3 is perfectly satisfactory, it may be undesirably complex to implement since it requires that the light beam is precisely aligned with the lines of the deposited pattern throughout the writing step. Any misalignment produced by, for example, a misplaced substrate or imperfect programming or operation of the scanning apparatus, can leave unpolymerised polymer, and produce walls of reduced and/or uneven width.

Figure 4:
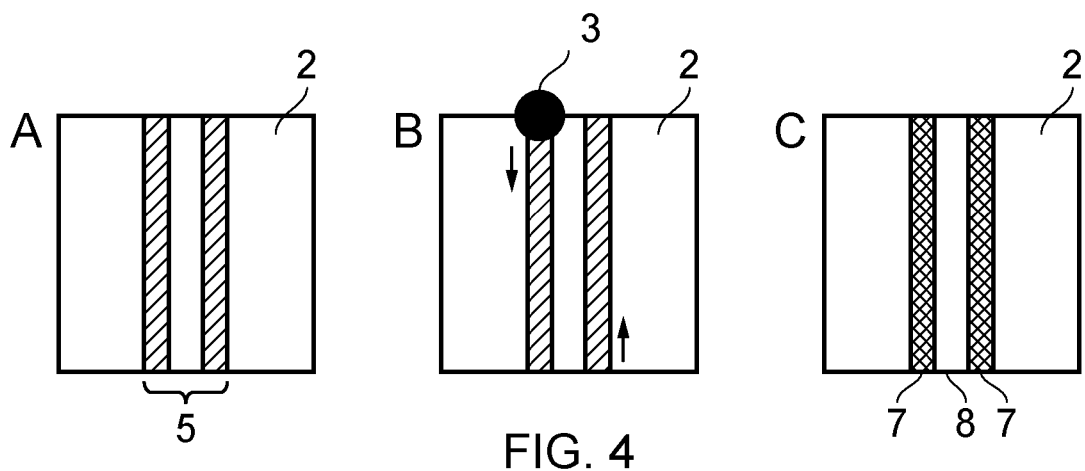

FIG. 4 illustrates steps in an alternative embodiment that reduces this complexity. FIG. 4A shows in schematic plan view a substrate 2 having the same polymerisable substance pattern 5 of a pair of parallel lines as shown in FIG. 3A. FIG. 4B similarly shows the substrate 2 ready for laser writing, with the light beam 3 aligned for movement along a first line in the pattern 5. In this example, however, the light beam 3 has a width which is greater than the width of the individual lines in the pattern 5. Again, the light beam is written along the lines as indicated by the arrows, to polymerise the polymerisable substance. However, because the light beam 3 is wider than the lines, it overlaps each line at each side as it moves along that line. The polymer line is hence polymerised across its full width, but alignment between the light beam and the line need not be very precise to achieve this. Any deviation of the centre of the light beam spot 3 from the midpoint of a line is not critical; the light can still expose the full width of the line (although one may need to take account of any varying intensity profile across the beam, for example in case of a Gaussian profile, to ensure complete polymerisation through the thickness of the substrate over the intended line width. This can be however avoided by using homogenised beams with uniform spatial profiles). The larger the light spot, the greater the errors in alignment which can be tolerated. However, increasing the light spot diameter will decrease its intensity and hence the amount of light energy delivered to the polymer, so the light spot size will need to be balanced against the need to deliver sufficient energy for polymerisation. A slower scanning speed might be used to compensate for a larger spot size. FIG. 4C shows the substrate 2 after the scanning. As with FIG. 3C, the lines are polymerised across their full width to form the walls 7 of the channel 8, but this has been achieved at a lesser alignment precision. Hence, a larger beam size may be preferred.

Note that in the example of FIG. 4, the light beam overlaps the edges of the lines in the pattern, in other words, the light exposure extends past the edge of the polymer line and onto the plain substrate material. This overlap may help to ensure that all edge parts of the polymer are hardened. Other arrangements of overlap can also be used to achieve this effect.

Figure 5:
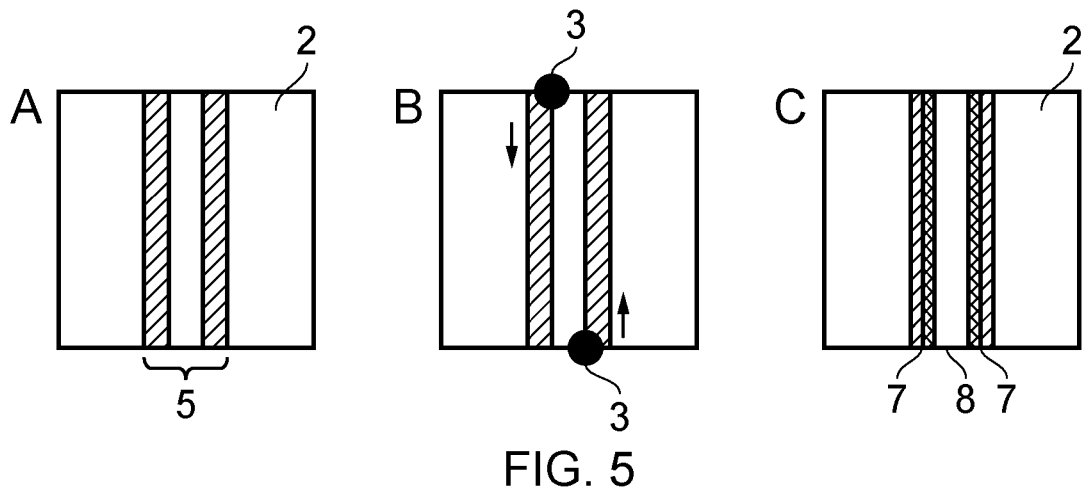

FIG. 5 shows steps in a further alternative embodiment, which uses a different overlapping arrangement between the light spot and the patterned lines. FIG. 5A shows a schematic plan view of a substrate 2 having a pattern 5 of lines of polymerisable substance deposited on it. FIG. 5B shows the substrate 2 ready for the light exposure step, where the light spot will be moved along each line of the pattern 5, for example as indicated by the arrows. In this example, though, the light beam is aligned with a first line in the pattern 5 so that it overlaps the inner edge of the line only, the inner edge being the edge adjacent to the intended channel interior and hence also the edge proximate to the other line in the pair. The outer edge of the line, remote from the channel interior and the other line, may not receive any light exposure. In other words, the line extends beyond the width of the light beam 3 in the outer direction. The second line is then written over in the same manner, so that the light beam 3 overlaps its inner edge only, this being the edge proximate to the first, already written line. To achieve this overlapping alignment, the light beam 3 can have any width, and in particular can be narrower than the width of the lines. In other words, the width of the light beam in the direction parallel to the width of the line can be less than the width of the line. This can be useful in achieving a higher light intensity, thereby enabling an increase in scanning speed, for example. FIG. 5C shows the finished substrate 2 after the light exposure. Since the light beam 3 overlapped the inner edges of the lines but did not extend to the outer edges of the lines, only an inner part of each line has been polymerised to form the channel walls 7. Note that "inner" refers to the edge of the line which is adjacent to the channel 8, that is, the side of the wall 7 intended to be in contact with the contained fluid. The same applies to lines defining fluid structures other than flow channels, such as reservoirs and wells, which can also be considered to have an "inner" edge in contact with the fluid, and an opposite "outer" edge away from the contained fluid. Using this partial overlap, unpolymerised material remains at the outside edges of the walls 7. However, since this is not within the channel and hence will not come into contact with fluid samples flowing in the channel, this residual radiation-sensitive substance is not problematic. A particular feature of this overlapping arrangement in which only part of the pattern line width is polymerised is the ability to control the wall width to be narrower than either the light beam or the deposited polymer line. The wall width is determined by the width of the overlap between the light beam and the line, and can hence be freed from any width limitations that might be imposed by apparatus used to deposit the polymer pattern and shape the light beam spot.

Figure 6:
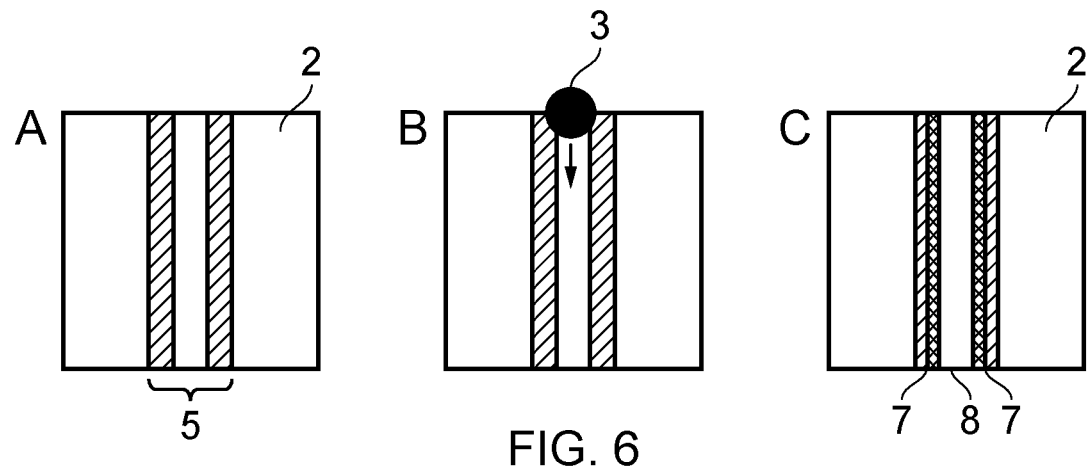

FIG. 6 shows schematic plan views of a substrate undergoing stages in another embodiment of the method, which again uses an overlapping arrangement. As in FIGS. 3, 4 and 5, FIG. 6A shows the substrate 2 with its deposited pattern 5 of polymerisable substance, and FIG. 6B shows the substrate ready for the light writing stage, with the light beam 3 aligned for scanning along the lines. In this example, the light beam 3 has a width orthogonal to the channel length and the direction of light beam movement which is greater than the width of the spacing between the pair of lines that will form a channel. The light beam 3 can therefore be aligned so that it overlaps the inner, proximate, edges of both lines in the pair of lines at the same time. The outer parts of the light beam 3 overlap the inner edges of the lines, and the beam 3 is translated along the pair of lines, rather than along a single line as in the previously described embodiments. Both lines of the pair are hence exposed simultaneously, and a channel can be formed by a single traverse of the light beam 3. Total time for the light exposure stage for forming a channel can therefore be roughly halved, giving more efficient manufacturing. FIG. 6B shows the light spot 3 with a width which is greater than the line spacing but less than the total width of the line pair. Hence, the outer edges of the lines are not exposed and polymerised. Consequently, the finished substrate, shown in FIG. 6C, has a similar structure to that of FIG. 5C, in that the walls 7 are formed from the inner parts of the lines only, and unpolymerised material remains at the outer edges of the lines. However, the channel has been formed with only one scan of the light beam instead of two. As in FIG. 5 example, the width of the finished walls 7 can be controlled by selection of the size of the overlap between the light beam and the inner parts of the lines.

The example of FIG. 6 is not limited to the beam width illustrated, being a width less than the total width of the line pair. A greater beam width can be used, which may be equal to or greater than the total width of the line pair, with the light beam aligned at or near the centre point of the space between the lines. In this way, both lines in a pair can be polymerised across their full width with a single light exposure scan. This convenience and increased production speed will need to be balanced against the likely lower light intensity available for the larger light spot size, which might require a reduced scanning speed. However, for especially narrow channels, a single light beam exposure for both walls may be found very beneficial.

Also, a light beam width which is large compared to the pattern line width may be useful for exposing small or tight details in the deposited pattern without the need to follow the line too closely; several small details in the deposited pattern can be encompassed within the light spot at one time.

Depositing the Radiation-Sensitive Substance

Any technique which is capable of depositing the radiation-sensitive substance onto the substrate surface in a desired pattern of lines can be used for the present invention. Of particular application is the technique of ink-jet printing, which can provide very fine detail and narrow line widths and spacings in an endlessly repeatable manner while also being easily adjustable to print different patterns. For example, current ink-jet printing techniques may print features of 10-30 µm or smaller. Commercial ink-jet printers can be readily modified to print with polymerisable substances, photoresists and other radiation-sensitive substances in place of inks, or purpose-built ink-jet printers might be used if preferred.

In some embodiments of the invention, the depositing stage may be performed and completed before the radiation is applied. For example, multiple substrates might be sequentially or simultaneously subject to inkjet printing to have their line patterns deposited, and then the multiple substrates may be exposed to radiation individually or in batches.

Alternatively, the depositing and the application of radiation may be performed in a combined step, with the application of radiation beginning on a substrate before the depositing for that substrate is complete. A way to achieve this is to provide a radiation-sensitive substance delivery system, such as an inkjet printer head, and a radiation beam delivery system, such as a laser or optical fibre delivering light from a laser plus mirrors and/or lenses to focus (if a focussed beam is used), shape and direct the beam, on a common assembly. The assembly and a support for the substrate are configured for relative translation. By arranging the radiation-sensitive substance delivery system in front of the radiation beam delivery system and moving in the correct direction, the radiation-sensitive substance can be deposited onto the substrate shortly before the radiation beam is applied onto it. Sideways movement of one or both delivery systems may be required to accommodate the formation of continuous walls with bends or corners, to maintain alignment of both delivery systems with the desired pattern line. An advantage of such an arrangement is that the required alignment between the deposited lines and the radiation beam is determined by the common assembly so will be fixed consistently for every substrate, and can be easily corrected by adjustment to the common assembly.

Figure 7:
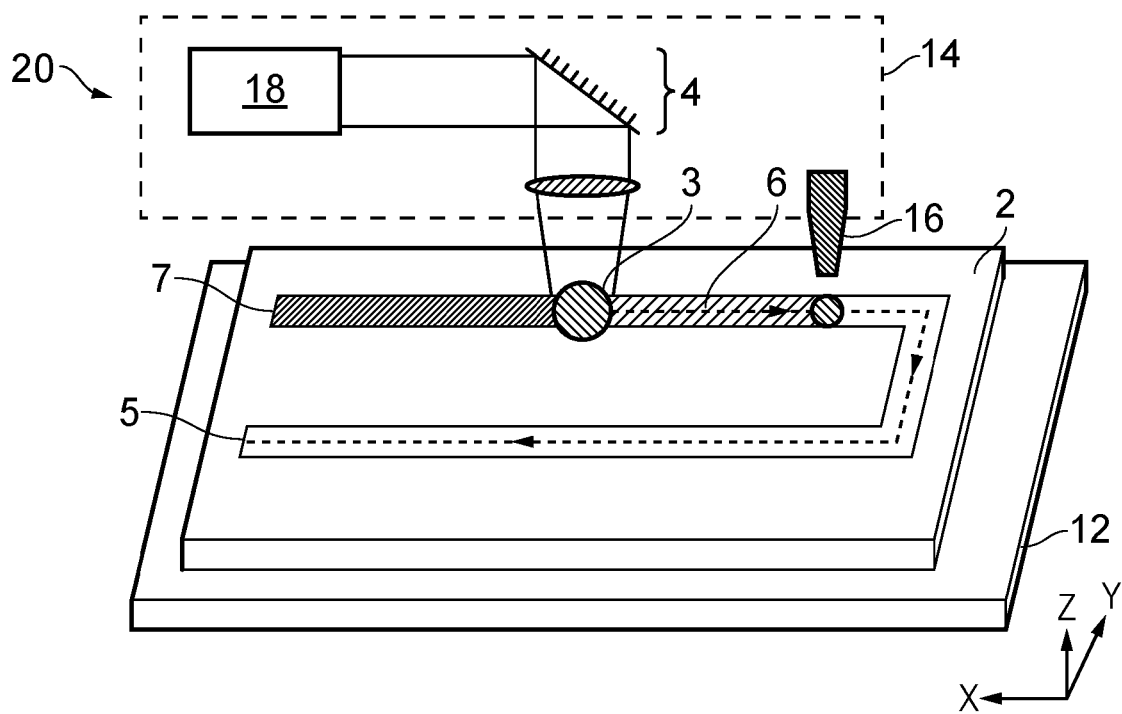
FIG. 7 shows a simplified schematic perspective view of apparatus for performing a method according to a further embodiment of the invention.

FIG. 7 shows a schematic perspective view of an apparatus configured to perform this embodiment of the invention. In this example, the radiation is a laser beam, but it will be appreciated that other sources of radiation could be used. The apparatus 20 comprises a platform or other support 12 for holding a porous planar substrate 2 in the X-Y plane during processing (via clamps, a vacuum manifold, or any other fixing means, not shown), and a common delivery assembly 14. The platform 12 and assembly 14 are arranged for translation relative to one another in the X-Y plane such that the substrate can be moved relative to commodities delivered from the assembly. Also, translation of either or both of the platform 12 and the assembly 14 along the Z-axis (orthogonal to the plane of the substrate) can be used to position the substrate 2 at the focus of the light beam 3. Movement along the Z-axis might also be used to adjust the size of the light beam 3 illuminating the substrate 2, thereby changing the area of the substrate surface which is exposed at any time. Either or both of the platform 12 and the assembly 14 may be movable, preferably under control of a computer processor (not shown) so that the movement may be programmed and is thereby both repeatable and readily modifiable.

The common assembly 14 is arranged above the platform 12 and the supported substrate 2 and holds a radiation-sensitive substance delivery system 16 in the form of (in this example) an inkjet printer head configured to deposit a radiation-sensitive substance from a reservoir (such as a cartridge) onto the substrate surface. A light delivery system is also carried on the assembly 14, to direct a light beam 3 onto the substrate surface. The light beam is provided, in this example, by a laser 18, and directed and focused to the desired spot size and intensity by a mirror and lens 4 (more complex beam shaping arrangements may be employed). The laser 18 may be mounted on the assembly 14, or may be held elsewhere and its light provided to the mirror and lens 4 by an optical fibre or through free space.

The two delivery systems are arranged on the common assembly such that relative translation of the assembly and the substrate substantially along an axis joining the two delivery systems causes a given spot on the substrate to be firstly aligned with the radiation-sensitive substance delivery system and then with the light beam delivery system. Required sideways motion of one of the delivery systems (motion not along the path of the line being written) to accommodate curves in the line can be easily provided by adjustment of mirrors and lens directing the light beam, for example. In this way, the substance deposited on the substrate surface is shortly thereafter exposed to the light beam and converted to a less permeable state. In FIG. 7, a desired pattern 5 in the form of a line is indicated on the substrate surface. By translating the substrate 2 (or the common assembly 14) along this line, radiation-sensitive substance 6 is deposited from the inkjet printer head 16. The deposited material 6 is then passed under the light delivery system and is hence exposed to the light beam 3 to be hardened into a wall feature 7. A second line spaced apart from the first will then need to be written to define a flow channel. For implementation of an embodiment such as that of FIG. 6, in which both lines in a pair are converted to the less permeable state together, the common assembly 14 can carry a pair of spaced apart printer heads 16; preferably the spacing can be adjusted to form channels of different width. Similarly, the light beam width and intensity should be adjustable, and also the speed of the relative translation.

The term "common assembly" is not intended to be limited to a same physical structure carrying both the delivery systems. Separate structures might be employed. The purpose of the assembly is to support the two delivery systems in known alignment to each other relative to a direction for the relative movement between the substrate and the delivery systems; any structure performing this function can be employed.

The depositing step is not limited to inkjet printing. Other techniques which might be used include spray printing, other nozzle-based arrangements, and lithographic techniques.

Reagents

For fluid flow devices intended for medical, biological and chemical diagnostics, one or more reagents are deposited onto or embedded into the substrate. A fluid sample is applied to the device and flows along one or more flow channels to a reagent site where it reacts with the reagent(s). The stage in the device manufacturing process at which the reagent is included in the device may vary depending on the particular application. For some applications, the stage is not of great importance. An advantage of depositing a localised pattern of the radiation-sensitive substance is that there is a smaller area in which the substance can come into contact with the reagents and so undesirable interactions between the radiation-sensitive substance and the reagents can be reduced or avoided altogether. Compare this with the known laser-writing technique [19], in which the substrate is completely impregnated with radiation-sensitive substance before the writing step, and then immersed in solvent to remove unpolymerised material in the development step. Under such a process, addition of the reagent will typically have to be done after these stages. The present invention is more flexible, and allows the reagent to be added at an earlier stage, if desired. In particular, biological reagents can be damaged by exposure to ultraviolet light, so if the present invention is implemented using radiation with a wavelength in the visible light region of the electromagnetic spectrum (good results have been produced using visible blue light at 405 nm wavelength, for example) or infrared parts of the spectrum, any reagent, even those prone to ultraviolet damage, can be added before the radiation exposure. This might be done as part of the deposition stage, so that the reagent and the radiation-sensitive substance are printed or otherwise deposited onto the substrate at the same time, or in a same step. The common assembly in the apparatus shown in FIG. 7 might be modified to include a further printer head 16 to deposit a reagent, for example. Reagents which are not affected by the particular light wavelength used can be applied to the substrate at any time, either before or after the light exposure.

Device Types and Configurations

Clearly, a wide range and variety of flow devices and structures on porous substrates can be fabricated using the methods described herein. As mentioned, the shape of the fluid-containing regions is limited only by the available ability to print or otherwise deposit a particular pattern of lines. The lines can define any type and variety of regions, including channels along which fluid may flow and which may have a fixed or a varying width and follow straight, spiral or serpentine paths. Reservoirs, wells and the like may also be used. These may be self-contained for confining received fluid (in the manner of a microtiter plate, for example), or may be connected to other regions by one or more channels, to give a fluid flow network. A single substrate may include more than one network, or multiple self-contained regions. Any number of sample or analyte introduction locations can be connected to any number of test zones or locations via any number, shape and pattern of flow channels.

As discussed above, it is possible to form walls which are fully impermeable to the fluid and extend through substantially the full thickness of the substrate, by depositing radiation-sensitive substance which extends right through the substrate, and exposing that substance to sufficient light energy to solidify it through the full substrate thickness. However, the invention is not so limited, and may also be used to form barriers within flow channels and other fluid-containing regions which are partially permeable. Such barriers, being volumes of solidified polymer within a flow channel which extend through only part of the substrate thickness, or which extend through the full thickness but are in a partially permeable state, can be added to any of the channels or other network structures to control flow within the channels, where the barriers may have a substantially constant thickness to reduce fluid speed, or may have a thickness variation along the flow direction to produce one-directional flow. Varying depth barrier profiles can also be used for delay alone. Thus, the barrier, by forming an obstacle within a flow channel, acts to impede the flow of fluid past the barrier. According to embodiments of the invention, partial barriers of this type can be formed by depositing radiation-sensitive substance onto the substrate within a region intended to receive fluid (such as between the walls of a channel) and applying sufficient light energy to cause hardening through only part of the substrate thickness. This can be achieved by depositing the radiation-sensitive substance such that it extends only partly through the substrate thickness and then fully solidifying all of that substance by light exposure, or by depositing the radiation-sensitive substance to extend through most or all of the substrate thickness and solidifying only part of the thickness of the substance by applying a reduced amount of radiation. The former technique may be preferred since it may leave less residual unsolidified polymer within the fluid network. Alternatively, the porosity of a barrier can be controlled depending on the radiation energy used, to provide varying degrees of delay to fluid flow. A partial barrier can be defined by a particular line of the deposited pattern that occupies an area within a region intended for fluid, so that both full thickness walls and partial barriers can be formed by a single application of a method according to the invention. Alternatively, the method may be used to create partial barriers only, perhaps within an existing fluid network already fabricated in a substrate by any technique. The structure and use of partial barriers is explained further in GB1408303.4 (although the barriers are made by a different technique).

As discussed above, the pattern of radiation-sensitive substance may be deposited on the surface of the substrate and then may spread through the thickness of the substrate so that when converted to the second state under the application of radiation, the radiation-sensitive substance forms less permeable walls or barriers within the substrate.

However, it is also possible to form structures on the surface of the substrate using the present technique. For example, when the radiation-sensitive substance is deposited, while some of the substance may soak through into the substrate, a film of substance may remain on the surface of the substrate for some time after depositing the substance. If the radiation is applied while there is still a pattern of substance remaining on the surface of the substrate, then when the radiation is applied the surface substance will also be converted to the second state, forming "bumps" which project above the surface of the substrate. This can be useful, for example, when wells or channels are formed within the substrate for containing or guiding fluid, as the surface bumps can prevent fluid spilling out of the wells or channels over the surface of the substrate.

Devices may be extended from two-dimensional flow networks. For example, by forming a particular structure in a paper (or other porous) substrate, it is possible to make a three-dimensional network by then folding the paper along pre-defined fold lines. The folds will bring various parts of the structure into juxtaposition, and new channels can be formed across the layers of paper since fluid can soak or wick from one layer into the next layer within the boundaries set by the barrier walls. The intended fold lines may be marked onto the substrate surface, perhaps by printing, to facilitate the folding. This allows more complex microfluidic networks to be created, and also facilitates distribution of complex devices in a simple manner, since substrates can be delivered unfolded, then folded for use by the end user.

In other examples, a three-dimensional network can be formed by stacking multiple substrates, each of which having a fluid flow network formed using the method described above. For example, vertical channels passing through the thickness of the substrate to allow fluid to flow from one layer of substrate to another may be bounded by walls formed by converting the radiation-sensitive substance to the impermeable state on exposure to radiation, and horizontal channels passing orthogonal to the thickness of the substrate within one layer of substrate may be bounded by walls formed in one or both adjacent layers of substrate.

A colour change caused by the reaction between analyte and reagent at a test site on a device can be employed to encode the result of the test such that it can be read automatically, or only understood by a healthcare professional. For example, the substrate may be printed with a one- or two-dimensional pattern similar to a bar code or a QR code. A colour-change reagent may be embedded at one or more locations within the pattern in a colourless manner; these are connected to an analyte introduction site elsewhere on the substrate by one or more channels. Analyte introduced onto the substrate will flow to the test location(s), and possibly cause a colour change at the location(s) depending on a positive or negative test. The colour change will alter the shape of the pattern, which can then be read by a hand-held scanner or photographed by a mobile telephone or tablet camera for communication to a remote diagnostic facility or website, and interpreted accordingly. Other information, such as type of test, and patient identity, could be encoded in the test pattern also, to further facilitate automated testing.

Fluid flow devices according to embodiments of the invention are not limited to medical applications such as diagnostics. Biological and chemical sensors in lateral flow test formats for sample testing are also required in fields including veterinary medicine, the food, beverage, water and pharmaceutical industries, agriculture, environmental sensing, and defence & security applications. The invention can provide devices for use in all of these fields, and any other requiring fluid sample testing.

Substrates

A variety of materials may be employed as a substrate for the present invention. Typically, the substrate will be planar, such as a sheet or layer of material. Paper has been found to be of particular interest, since it is readily available in a range of thicknesses, densities, porosities and colours, is inexpensive, can be easily cut to size, can be printed with instructions, directions and indicia, can be folded, and is lightweight. However, other porous materials may be used instead, such as cardboard, or woven and non-woven fabrics made from natural or synthetic fibres and combinations thereof. The substrate material should be able to withstand exposure to the required radiation energy density without suffering unacceptable ablation or other damage, and be able to undergo any subsequent processing steps needed to produce the finished device. A material which displays these characteristics may be used as the substrate in the present invention. The properties and characteristics of potential substrate materials can be compared when selecting a potential substrate for a particular device. A property of particular interest is the density of the material as expressed through its internal structure, or its pore sizes, since this will affect the size of the solid structures which may be written into it. A material with an open structure (such a large-grained paper with wide grain spacing) may have a minimum barrier width that is able to fully contain fluid within a region, so that thinner structures cannot be used on such a substrate. This may affect the overall minimum device size which is achievable.

Another substrate material of special interest is nitrocellulose, such as in a sheet or membrane format. Nitrocellulose membranes have particular application in point-of-care biosensor devices (such as pregnancy tests) since the material has a range of advantages. It has a high binding affinity for proteins, it produces only a low background signal, and is compatible with a variety of detection methods including chemiluminescent, chromogenic and fluorescent techniques. Also, the manufacture of nitrocellulose, which is well-established at the industrial scale, can be controlled to produce pores of specific sizes which are large enough to allow fluid flow as required by the present invention.

Other examples of substrates may include sintered materials such as sintered glass or sintered plastics.

Some substrate materials may have wicking ability, which can be useful because this allows a fluid to be drawn along a channel in the required fluid flow and the radiation-sensitive substance can be drawn down through the substrate thickness in the deposition stage.

Other materials may not have an inherent wicking ability, and instead the fluid flow may be controlled by the application of an external factor, such as an electric field or exposure to radiation. This can be useful for example because the fluid flow device may take a fluid sample at the point of care, but then may need to be inserted into a device reader or other apparatus in order to carry out the actual analysis of the sample. If there is a delay in transferring the device to the reader, then if the fluid naturally flows through the substrate, by the time the device reaches the reader the fluid may already have flowed through the fluid flow network and out of the device preventing appropriate analysis. This problem can be avoided if the fluid does not naturally flow through the substrate unless an external factor is applied.

For example, if the fluid is an ionic fluid, an electric field could be applied by the reader to trigger the flow of fluid.

Alternatively, if the fluid is not itself ionic, flow of fluid may be controlled by varying the wetting properties of the structures in the fluid flow network. For example, the wetting properties (e.g. hydrophobicity) of some materials may change when an electric field is applied or when electromagnetic radiation is applied. Such a material may be injected to coat the insides of the structures formed by the method above, so that they retain the fluid in an initial state and become more hydrophobic on application of the electric field or exposure to electromagnetic radiation, so that fluid starts to flow.

In some examples, different types of substrates can be joined to form a composite substrate, and then form the structures on the composite substrate using the method described above. This can be useful for providing different fluid flow rates in different parts of the composite substrate, for example.

Radiation Sources

The radiation applied in the method of the present technique may be any form of radiation capable of changing the deposited material from a first state to a second state, where the substance is less permeable in one of the first state and the second state than the other.

In one embodiment, the radiation comprises electromagnetic radiation. Electromagnetic radiation of any desired wavelength may be used. Preferred forms of radiation include ultraviolet radiation (typically defined as electromagnetic radiation having a wavelength of 20 to 400 nm) and visible light (typically defined as electromagnetic radiation having a wavelength of 400 to 700 nm).

Other sources of radiation may include ion beams, electron beams, and ultrasound, for example. Lasers provide convenient sources of radiation, since their beams can be focussed to a small spot size, a range of wavelengths are available, power can be easily adjusted, and beam scanning is readily implementable. However, other radiation sources may be used if preferred. For example, the radiation source may be a supercontinuum source, one or more light emitting diodes, or other source which is sufficiently bright and of the proper wavelength to produce the required transformation of the radiation-sensitive substance into the hardened state. The wavelength may also be selected having regard to the properties of any reagent to be provided in the fluid flow device, as discussed above.

The radiation spot as exposed onto the surface of the substrate can be produced by any arrangement which gives a spot of sufficient intensity or energy density to induce the state change in the radiation-sensitive substance. Often, this will be an arrangement such as focussing or imaging of the incident light beam which substantially reduces the spot size (while giving a spot of the required dimension for the line which is to be polymerised) so as to give a significant increase in the energy density of the beam. An unfocussed beam may be used instead, however. The light beam will generally be exposed directly onto the substrate surface to define the writing spot on the substrate surface, subject to any lenses, mirrors and the like used to form, shape and direct the light beam into the required spot size and shape. "Directly" indicates that there is no intervening mask or similar, such as is required in lithographic techniques.

The light source may provide a continuous emission of light or a pulsed emission, for example a laser source that produces regular or irregular pulses with durations on the nanosecond, picosecond or femtosecond scale. The terms "light beam", "beam", and "beam of light" are used in the context of the present invention to include both the continuous and pulsed alternatives.

It is also possible to apply more than one source of radiation to the same device. For example, sources of radiation of different types may be provided (e.g. ambient light and laser light, or ion beam radiation and laser light). Also, the different sources of radiation could provide radiation of different wavelengths, frequencies or energy density, for example. This can be used to provide further control of the formation of structures in the device. For example, the different sources may provide different depths or degrees of conversion of the radiation-sensitive substance from the first state to the second state, which can provide structures with different permeability to the fluid. For example, one source of radiation (e.g. a first laser) could be used to form walls and another source (e.g. a laser of different frequency or energy) could form barriers. In another example, the different types of radiation could for example correspond to different types of laser such as a pulsed laser and a continuous wave laser (see for example the experimental work below where pulsed and c.w. lasers can be used to form different kinds of barrier).

In some cases, the different sources of incident radiation may be applied in series so that a first source is applied initially, and later a second source is applied.

It is also possible to use simultaneous sources of radiation in parallel, so that multiple structures or barriers can be created at the same time. For example, a beam of radiation could be split into multiple beams each of which may be used to write a line, wall or barrier.

Experimental Work

Some experimental work is presented below. This work describes a particular example embodiment, but it will be appreciated from the above that the invention is not limited to this particular embodiment.

Figure 8:
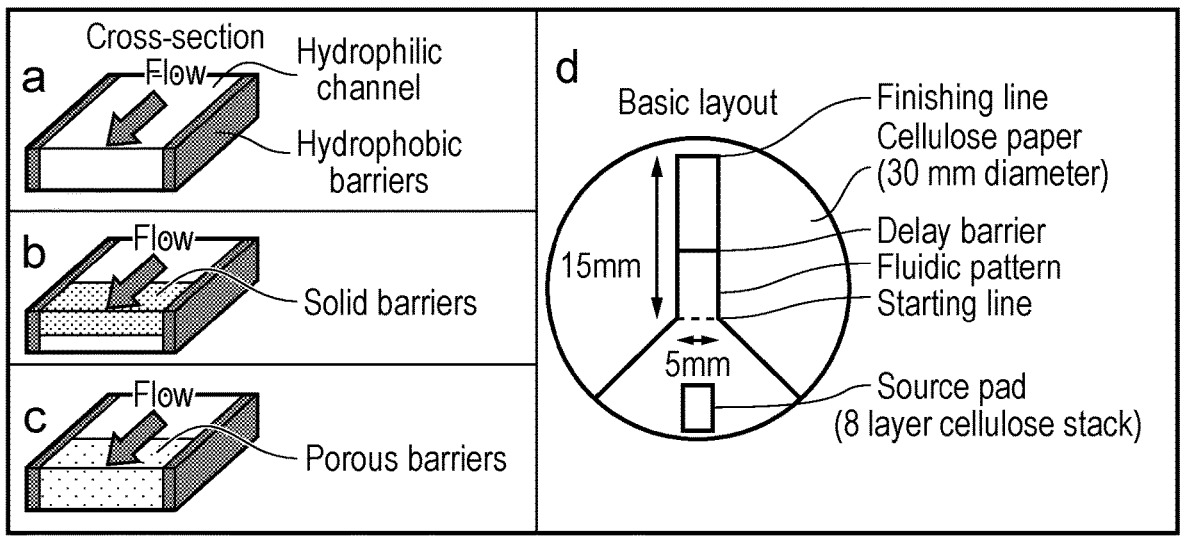
FIG. 8 is a schematic representation of some examples of fluidic structures used for experimental work.

FIG. 8 shows a schematic representation of: a) cross-section of a fluidic channel; b) cross-section of a fluidic channel with solid barriers; c) cross-section of a fluidic channel with porous barriers; d) layout of a pre-defined fluidic structure. The schematic in FIG. 8 shows a simple fluidic geometry that can be used to produce delay barriers via either of the two following methods, (1) by controlling the depth of solid or impermeable walls or barriers (as shown in FIG. 8b) that are patterned across the flow and which simply impede the fluid flow by reducing the height of the fluidic channel or, (2) by forming porous barriers (as shown in FIG. 8c) that allow controlled leakage of the fluids. As described and discussed in the later sections, the control over the depth of barriers of the first type or the porosity of the barriers of the second type is obtained by simply adjusting the laser-writing parameters such as the laser output power and scan speed. Unlike other paper-patterning methods, the approach presented here does not require any additional processing equipment or specialist materials and may use the same fabrication approach that defines the fluidic channels themselves.

Laser Setups and Materials

The lasers used for the laser directed writing (LDW) process were a Nd: $YVO_4$ laser (B M Industries, Thomson CSF Laser, France) operating at 266 nm, with a pulse duration of 10 ns, a maximum single pulse energy of 2 mJ, and a repetition rate of 20 Hz (used for method 1 as outlined above, and shown in FIG. 8b) and a 405 nm continuous wave (c.w.) diode laser (MLDTM 405 nm, Cobolt AB, Sweden) with a maximum output power of ~110 mW (for method 2, shown in FIG. 8c).

The paper substrates used were Whatman® No. 1 filter paper from GE Healthcare Inc. The photopolymer chosen for these experiments was Sub G, from Maker Juice, USA. The sample solution used for characterising the flow delivery delay was Tris Buffered Saline (TBS, 20 mM Tris, pH approx. 7.4, and 0.9% NaCl), which is a buffer commonly used in diagnostic assays.

Creating Fluidic Delays

We first patterned fluidic channels with the design geometry shown in the schematic of FIG. 8d. The width and length of the fluidic channel was 5 mm and 15 mm respectively, and the inlet end of the channel was designed to replicate the shape of a funnel. These fluidic channel patterns were defined using the c.w. (continuous wave) laser operating at 405 nm. We subsequently patterned the fluidic walls or barriers within the channels using either of the two lasers described previously. The channels were patterned using the c.w. laser due to the much higher writing speeds achievable (almost three orders of magnitude greater than that for the pulsed 266 nm source). To ensure that there was sufficient fluid to wick the entire length of the channel, we cut and stacked multiple (8 in this example) pieces of paper (of 3 mm×5 mm), and positioned them at the wider end of the funnel-shaped inlet of the channel, and loaded it with a comparatively large volume of fluid (~40 µL)—the stack serving as a continuous reservoir of liquid.

Figure 9:
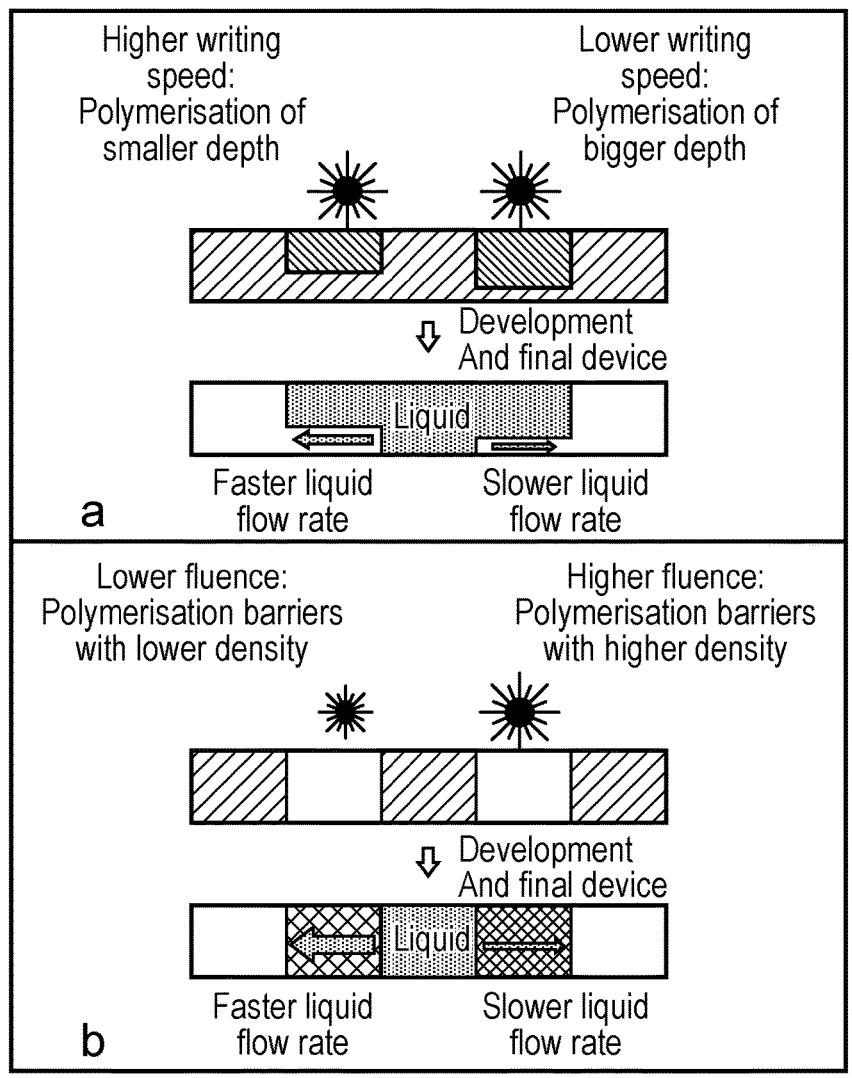
FIG. 9 is a schematic of an example of fabrication of barriers of variable depth or degree of polymerisation.

FIG. 9 shows a schematic of the fabrication of (a) polymerised walls or barriers of variable depth inside the paper substrate; b) barriers of variable degree of polymerisation extending throughout the full thickness of the paper. Both methods allow for controlled wicking, and variable flow delays.

During our studies into the fabrication of fluidic channels using pulsed laser irradiation, we observed that by controlling the scanning speed (and therefore the effective exposure) of the laser beam, we could polymerise lines of various depths inside the paper substrate as illustrated schematically in FIG. 9a. Slower scanning speeds produced polymerisation through the full depth of the paper, while faster scanning speeds led to photo-polymerisation only in the upper portion of the paper, thus creating partial barriers that the liquid was able to overcome. These fluidic 'delay barriers' can therefore decrease the liquid flow by a rate that is proportional to their depth, and hence this principle can be used to impose a user-defined variable time-delay in the wicking of the liquids and test samples.

An alternative approach, as illustrated in FIG. 9b allows the writing of barriers via manipulation of the extent of polymerisation using c.w. laser exposure. In this case however, the barriers produced extend throughout the full paper thickness, but the degree of polymerisation can be engineered to form barriers whose porosity can be controlled. For these less dense, leaky barriers, the polymerised material does not completely fill the voids within the paper matrix, and instead the polymerised material simply coats the fibrous strands, without forming a completely impermeable barrier.

Figure 10:
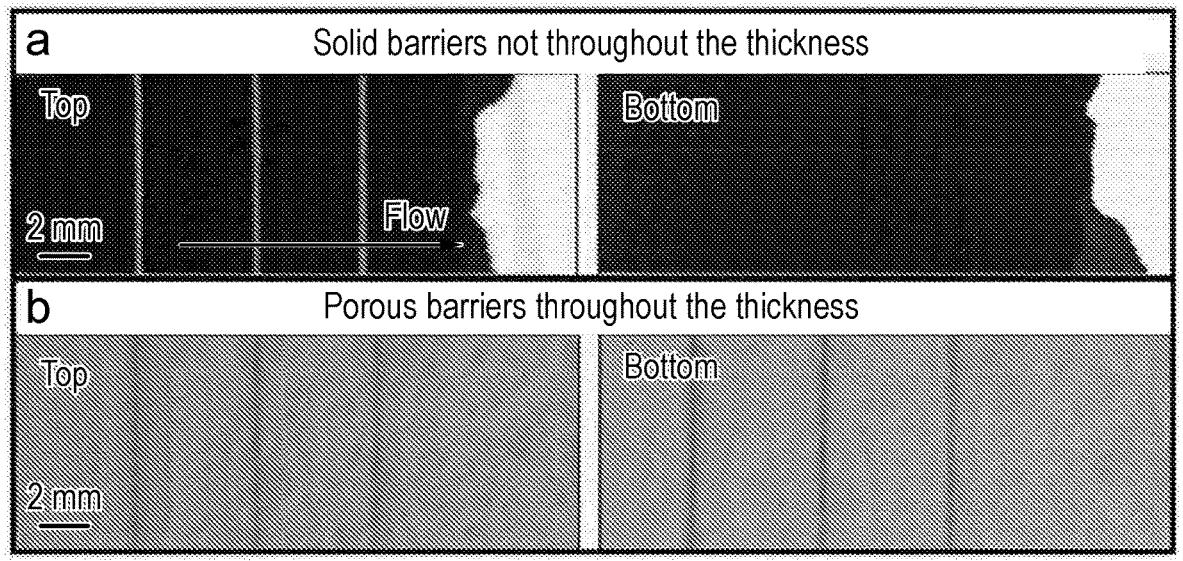
FIG. 10 comprises some images showing delay barriers from both sides of a substrate.

FIG. 10 illustrates the difference between such barriers. FIG. 10 comprises images showing the delay barriers from both sides of the cellulose paper. a) Depth-variable impermeable barriers through part of the thickness of the substrate, formed by pulsed laser exposure; b) porosity-variable barriers formed by c.w. laser. As shown in FIG. 10a, the polymerised regions for barriers written with a pulsed laser could only be observed on the top, and not the bottom face, suggesting partial polymerisation through the thickness of the paper. However, the polymerised regions for porous barriers written with a c.w. laser always extended throughout the entire paper thickness, as shown in FIG. 10b.

As described below, we compare both of these methods for generating controllable flow delay in fluidic channels. The study was aimed at characterising the influence of the laser fluence and exposure on the depths and porosity of the barriers for methods 1 and 2 respectively, including an investigation of delay as a function of positions and numbers of barriers. Since both the fluidic channel (walls) and delay barriers can be patterned using the same LDW process, this technique should have immediate appeal to manufacturers wishing to develop such paper-based devices on a large scale where production speed and cost are two of the main considerations.

Results and Discussion

Method 1: Delay via solid barriers created by pulsed laser writing.

Figure 11:
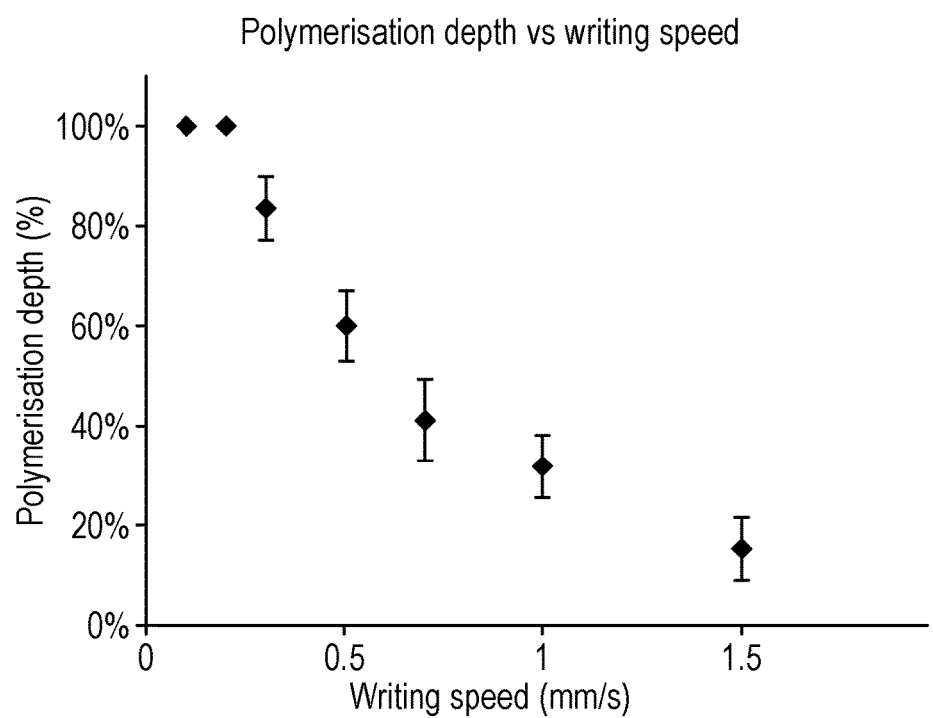
FIG. 11 is a graph plotting the depth of polymerisation against writing speed.

In order to explore the relationship between the depth of the barriers and the incident fluence, which depends on both the laser average power and the laser scan speed, we first fabricated a set of polymerised barriers written with a fixed incident average power (7 mW) but different speeds from 0.1 mm/s to 1.5 mm/s. We then measured the depth of these barriers by cutting the paper substrates along a line that intersects the barriers, and then imaged the cross-sections of the paper using an optical microscope. The relationship between the depth and the barrier writing speed is plotted in FIG. 11, which shows that an increase in the writing speed from 0.3 mm/s to 1.5 mm/s leads to an decrease in the depth of the barrier from ~90% to ~10% of the thickness of the paper. Error bars indicate the standard deviation for 3 measurements.

Figure 12:
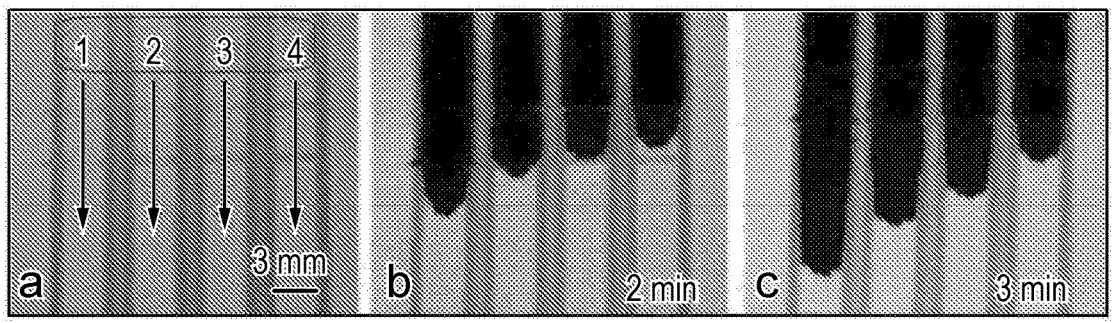
FIG. 12 shows the delay of fluid flow in fluidic channels with barriers created using different writing speeds.

FIG. 12 is an image showing the delay of the liquid flow after introduction of blue ink in fluidic channels with barriers created using different writing speeds. To understand and quantify the usefulness of these solid barriers with variable depths in both delaying and even completely stopping the fluid flow, we fabricated a set of 4 channels, as shown in FIG. 12, and then patterned barrier lines perpendicular to the flow direction. Each of the fluidic channels was inscribed with two barriers, both of which had been written under the same writing conditions. Importantly, for each of the fluidic channels (1-4) these pairs of horizontal lines were written with the same incident average power (7 mW) but different speeds namely, 1 mm/s, 0.7 mm/s, 0.5 mm/s and 0.3 mm/s, thus forming solid barriers with differing depths, which can be calculated from the plot in FIG. 11.

As shown in FIGS. 12a and 12c, coloured ink introduced from the inlet of the channels, (marked in the image) experiences a flow rate that is a clear function of the presence and strength of the inscribed barriers, with channel 4 being the slowest, and channel 1 the fastest. The ink was introduced at the same time in each of the four channels. FIGS. 12b and 12c are images taken 2 min and 3 min after the introduction of ink, and as seen in FIG. 12b, the ink has already flowed past the two barriers of channel 1, is leaking past the second barrier of channel 2, has just reached the second barrier in channel 3, while it has just crossed the first barrier in channel 4.

Figure 13:
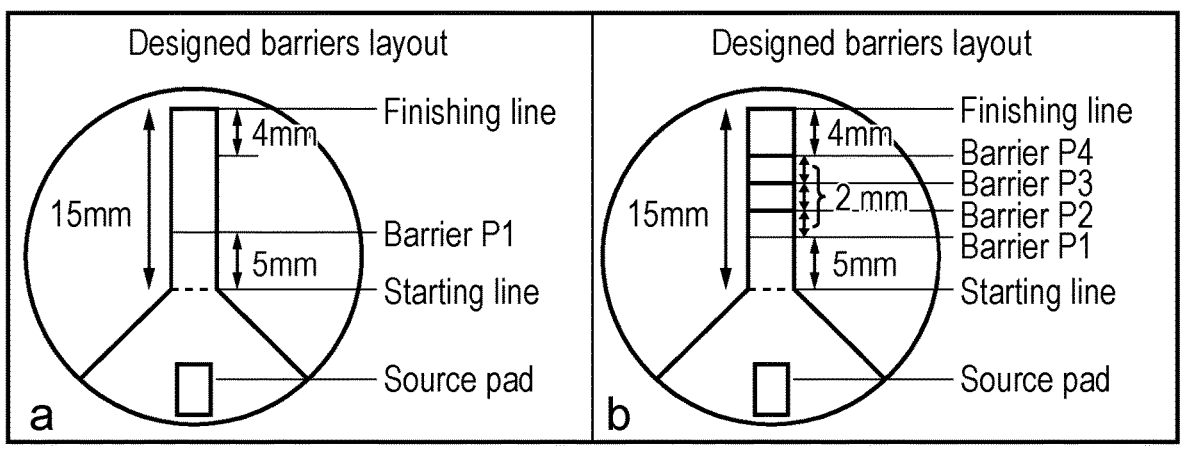
FIG. 13 is a schematic representation of a designed barrier layout showing the position of various delay barriers.

FIG. 13 is a schematic representation of designed barrier layout showing the position of delay barriers (P1, P2, P3 and P4). To quantify the flow delay versus writing conditions, we used the arrangement of FIG. 8(d), which is shown in greater detail in FIG. 13, using TBS (pH=7.4), a reagent conventionally used as a buffer in bio-chemical assays, as the liquid medium. The fluid 'delivery time' was defined and measured as the time the TBS solution needed to travel from the starting line to the finishing line, a distance of 15 mm in total. The channel walls were written with the 405 nm c.w. laser (20 mW, 10 mm/s), whereas the barriers were written with a pulsed laser at writing speeds from 1 mm/s to 0.3 mm/s.

First, we studied the consequence of having impermeable barriers with different depths in the flow-path, however, with only one delay barrier at position P1 (as shown in FIG. 13a) in each of the pre-defined device. Several devices, each with one single delay barrier were written under different writing conditions, by changing the scan speed (from 1 mm/s to 0.3 mm/s) at a constant laser average power of 7 mW, which corresponded to creation of solid barriers with depths ranging from ~20% to ~90% of the thickness of the paper (FIG. 12). We have quantified the ability of the barriers to delay the fluid flow using a normalised 'delay factor', which we define as the time to flow (from the starting line to the finishing line) in a channel that has barriers, divided by the time to flow in a channel without barriers:

$$\text{Delay factor} = \frac{\text{Flow time for a channel with barriers}}{\text{Flow time for a channel without barriers}}$$

Figure 14:
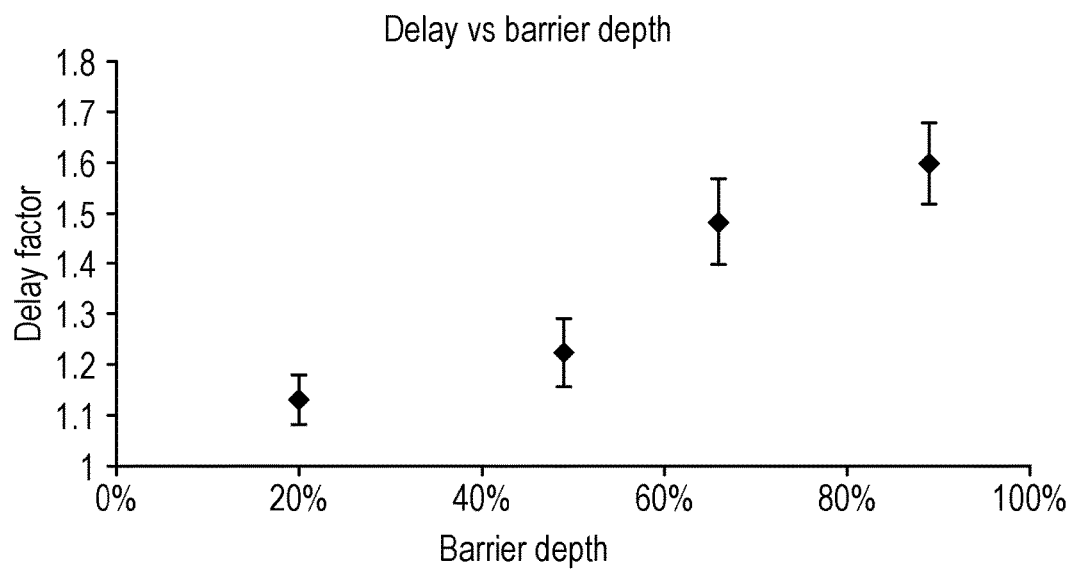
FIG. 14 is a graph plotting a delay factor against barrier depth.

The results for the delay factor are plotted in FIG. 14 which show an increase in the delay factor from ~1.1 to ~1.6 with an increase in the barrier depth from ~20% to ~90%. FIG. 14 shows the delay factor for devices with barriers having different depths. Barriers were written with different writing speeds at a fixed average power of 7 mW. Error bars indicate the standard deviation for 3 measurements.

Method 2: Delay using porous barriers created by a c.w. laser

In this case, both the fluidic channels and the flow delay barriers were written with the same c.w. laser (in a common programmed writing step) by simply changing either the laser output power or writing speed. To allow for a direct comparison with the results for the solid barriers, fluidic devices that were tested had the same design as in FIG. 13. In this case however, four porous barriers were written across the fluidic channels, to explore the role of number and position of barriers as shown in FIG. 13b. A comprehensive study was performed to explore the flow delay induced through barriers written with a range of different writing conditions. The fluid delivery time and the percentage-delay were calculated as for method 1.

We first did a comparative study for barriers patterned with different writing conditions, namely different laser powers and scan speeds. Subsequently, we then changed the number of the barriers to explore the relationship between the delay and the number of barriers in the flow path. As in FIG. 13b, a one barrier design/layout refers to a device with a single barrier patterned at position P1 in the channel; a two barrier device refers to a channel with two barriers patterned at P1 and P2; and so on.

Figure 15:
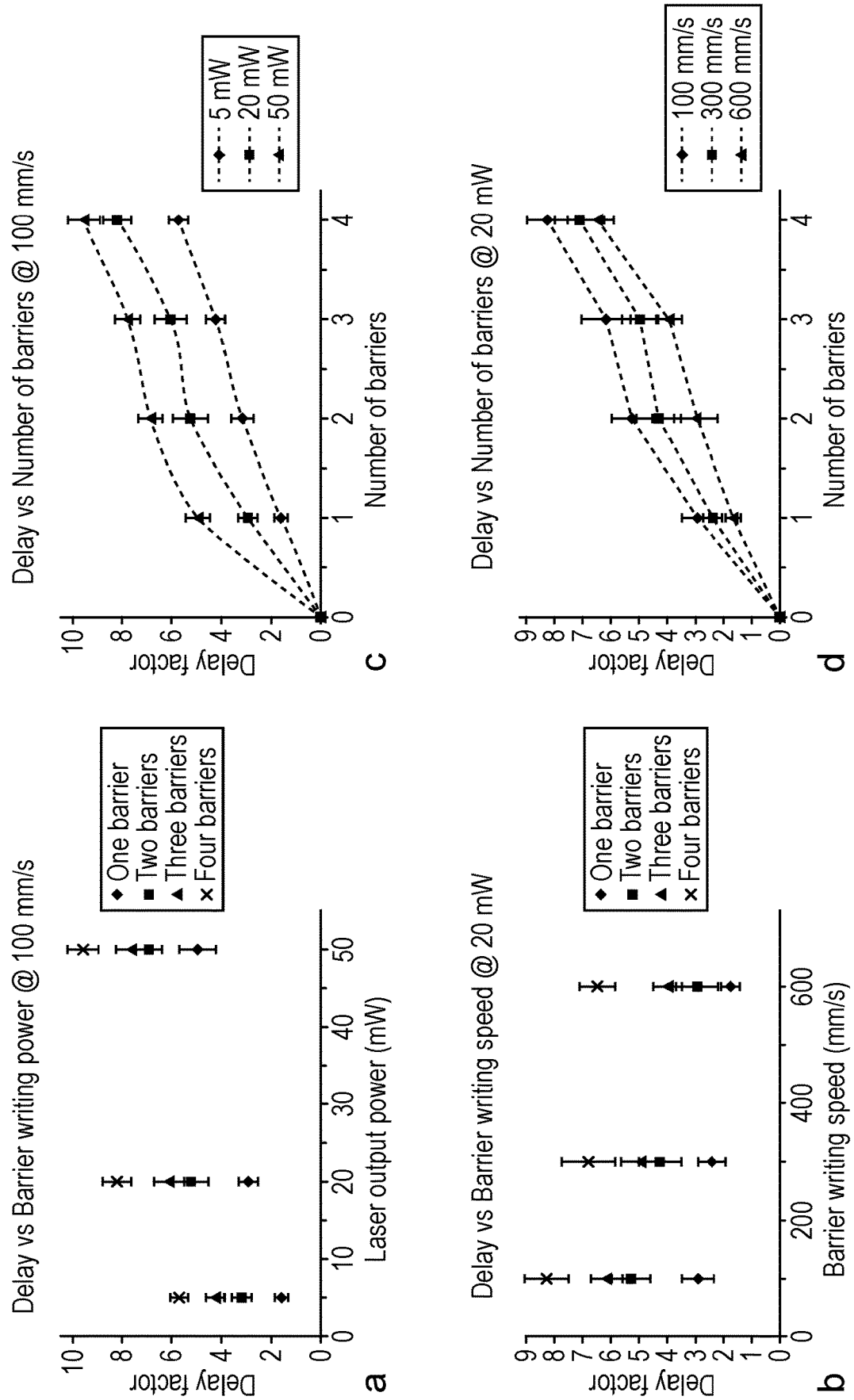
FIG. 15 comprises graphs plotting a delay factor against laser output power, writing speed and the number of barriers.

FIG. 15 comprises plots showing the delay factor of delay-barrier-designed devices. a) Barriers written with different laser output powers at a fixed scan speed; b) barriers written with different scan speeds as a fixed laser output power; c) different number of barriers written at a fixed scan speed; d) different number of barriers written at a fixed laser output power. Error bars indicate the standard deviation for 3 measurements, and lines are a simple guide for the eye.

As shown in FIG. 15a, for barriers written with a fixed scan speed of 100 mm/s, the fluid delay gradually increased with an increase of the laser power, and progressively decreased for barriers written with an increasing scan speed at a fixed laser output power of 20 mW, as shown in FIG. 15b. These results show that the porosity of these barriers is a clear function of the laser fluence used and that any targeted delay (within the experimental error) can be achieved by choosing the correct fluence. Similarly, for the plots shown in both FIGS. 15c and 15d, which are based on the use of multiple barriers, we observe identical trends—for barriers written with the same writing conditions, the delay increases with an increase of the number of barriers.

Figure 16:
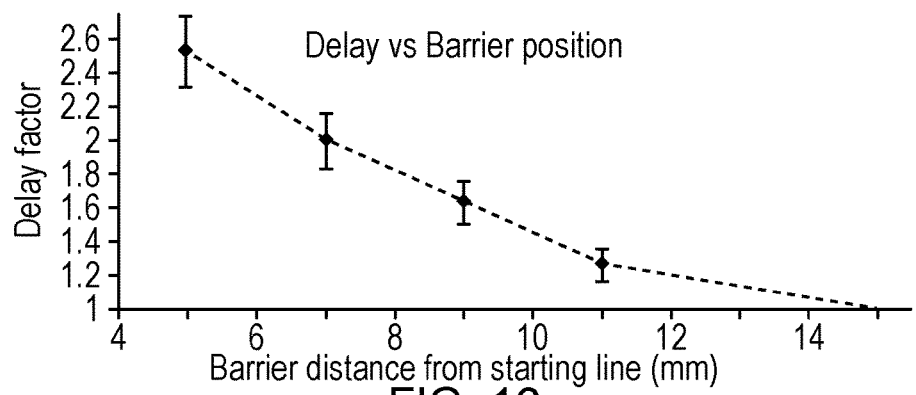
FIG. 16 is a graph showing the relationship between fluid delay factor and position of delay barriers.

In addition to this dependence on the porosity of the barriers and the number of barriers, we observed that the fluid delay also depended on the position of the porous barrier. FIG. 16 shows the relationship between the fluid delay factor and the position of the delay barriers (distance to the starting line) with the same condition of 200 mm/s scan speed and 20 mW laser output power. Error bars indicate the standard deviation for 3 measurements, and the line is a guide for the eye. We introduced a single porous delay barrier written under the same writing conditions (200 mm/s scan speed and 20 mW laser output power) at different positions (P1-P4) as show in FIG. 13b, and then studied the fluid delay. The plot of the fluid delay versus the position of the porous barrier is shown in FIG. 16. As the delay barrier was shifted further from the starting line towards the finishing line, the delay factor rapidly dropped from ~2.5 (for position P1) to ~1.3 (for position P4). We believe this is because of the geometry of the device, since the volume of the paper that serves as the reservoir for the fluid flow changes with a shift in the position of the delay barrier. The volume before the delay barrier acts as a pump for subsequent flow, thus affecting the flow rate after the barrier. As shown in FIG. 13b, the closer the barrier is to the starting line, the smaller the source volume is, and this leads, we suggest, to a lower pump force and hence a lower flow rate and larger fluid delay.

Multiple Fluid Delivery Using Delaying Barriers

Figure 17:
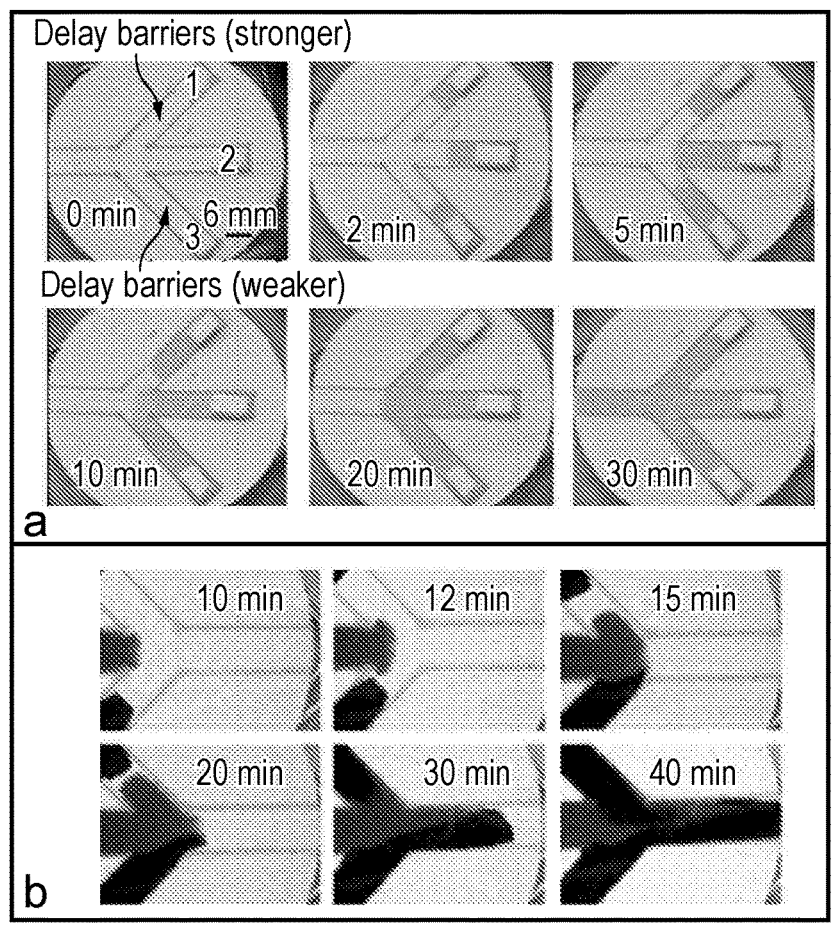
FIG. 17 shows a 2D multi-channel fluidic device for sequential delivery of three fluids.

Implementation of automated paper-based devices that are user-friendly and need minimal intervention from the patient or an unskilled user need strategies that allow control over the flow of several liquids (reagents and sample) along their pathways. Such devices allow the implementation of a multi-step assay, such as an ELISA (enzyme-linked immunosorbent assay), and in this section, using fluid delay strategies effected using the flow-barriers described earlier, we demonstrate the usefulness of our method to fabricate such automated paper-based tests. FIG. 17 is an image showing a 2D multi-channel fluidic device used for sequential delivery of three fluids. It has three identical channels (6 mm width and 23 mm length) modified with different delay barriers (1.Stronger delay barriers; 2.blank; 3.weaker delay barriers). a) Sequential images showing the arrival of BSA from each channel at different times; b) Sequential images showing the arrival and mixing of black and red ink from three separated channel and the subsequent mixing of the inks.

FIG. 17 shows a device that uses a network of three identical channels for sequential delivery of three fluids to a common detection or reaction point. As shown in FIG. 17, sequential delivery of each of these fluids is made possible by introducing (a set of three identical) porous barriers written with a c.w. laser across the fluid channels. By changing the porosity of the delay barriers through simple adjustments of the laser parameters, different delays can be introduced into each channel.

To show the operation of our devices, as also described earlier, we first introduced a source pad (a stack of 8 cellulose papers) into each channel that allows us to load a comparatively large volume of fluid (~40 µL) in to each channel, and also serves as a continuous reservoir of liquid (FIG. 17). We first tested the performance of our devices using TBS as the test-fluid which was introduced into the source pad in each of the three channels. FIG. 17a is a set of images that are snapshots taken sequentially at different times after introducing the TBS into the source pads. The fluid in channel 2 (that does not have any delay barriers) arrived at the intersection zone first (after 5 min) and continued to flow onwards until the fluid in channel 3 (with weaker delay barrier) arrived at the intersection (after 10 min). Thereafter, the fluids from these two channels mixed and flowed forward until the arrival of the fluid from the third channel (with the stronger delay barriers) after 20 minutes. Finally, the mixture of three fluids then wicks through the reaction pathway in the following 10 minutes.

To further illustrate the dynamics related to the mixing of the different fluids and to make the flow more obvious, we instead used three different coloured inks to source the three separate channels (black for channel 1 and 3 and red for channel 2). The sequential images that show the flow through the device are shown in FIG. 17b. When compared to the (blank) channel 2 that did not have any delay barriers, the fluid delivery through channel 1 and channel 3 were delayed by 15 and 5 minutes respectively. The results for both the devices that were either tested using TBS or the coloured inks though are evidence that our laser-patterned delayed-fluid flow strategy can be used to make paper-based automated devices. As a next step, we demonstrate the use of this strategy to fabricate devices that can implement multi-step ELISA protocols.

Automated Multistep Assay for CRP Detection by Sandwich ELISA

This section describes the use of our fluid delay strategy to implement a multiple step ELISA that enables the detection of CRP (C-reactive protein). We have chosen CRP as an example for evaluating this automated paper-based device because it is an important and realistic analyte which is frequently measured for early-stage diagnosis. Devices (with the 2D multi-channel geometries) identical to that shown in FIG. 17 were used to realise a multistep enzyme-based immunoassay that allowed for the detection of CRP. As shown in FIG. 18a, the three individual arms of the device were used to sequentially deliver the three different reagents—channel 1 delivered streptavidin-HRP; channel 2 delivered the sample; channel 3 delivered the detection antibody through to the capture antibody which was immobilized in the detection zone (identified in the image with a rectangular frame). As mentioned earlier, the device geometry and the delay mechanism used were the same as those in FIG. 17, except that an additional cellulose absorbent pad was attached at the end of the detection pathway for collection of the excess fluid.

The ELISA kit used in the implementation of the CRP detection (DuoSet® Human C-Reactive Protein/CRP) was purchased from R&D Systems, Inc. (UK). All the antibodies used were from this kit and were diluted to the working concentrations of 3.6 µg/mL and 162 ng/mL for capture antibody and conjugated antibody respectively. The CRP human standard (C1617) was purchased from Sigma-Aldrich (UK) and diluted to working concentrations using 1% BSA in PBS.

The capture antibody was pipetted at four distinct spots within the detection zone, and then left to dry for one hour at room temperature. The whole device was then immersed in a blocking solution (5% BSA in PBS) for one hour at room temperature, followed by three sequential washing steps using PBS. After subsequent drying, the device was ready to use.

In order to implement the assay, 40 µL of each reagent was simultaneously pipetted onto the source pads in each channel and the device was left in a covered petri dish at room temperature to allow for the timed, sequential delivery of the individual solutions along each channel, into the detection zone for reaction with the capture antibodies immobilized therein. After 30 minutes, the whole device was washed three times using PBS for five minutes each. Finally, the colorimetric substrate TMB (Tetramethylbenzidine) was added at the reaction zone and the result was read after 20 minutes. Ideally, such a device should also enable the sequential delivery of TMB to the detection zone via another fluid flow channel; however, for this initial proof-of-principle experiment where we intend to show the usefulness of delays, we have chosen not to do so. In case of several routinely employed assays, the detection antibodies are tagged either with a gold nanoparticle or coloured beads, and if we choose to use detection antibodies labelled in this fashion, then there would not be the need to have this additional delivery path. FIGS. 18b and 18c show the results for the detection of different concentrations of CRP, and the clearly visible and distinct four blue spots that appear in the detection zone (with minimal background colour 'noise') confirm the presence of CPR in the sample. FIG. 18d shows the result for a control device tested with a sample solution that did not have CRP. As shown in the figure, for this, negative result, we do not observe any specific blue spots in the detection zone. The colour intensity of the spots in FIG. 18b is greater than that in FIG. 18c, and this relates to the higher concentration of CRP in the corresponding samples that were used in the two different cases. For some of the spots, their non-symmetric circular shape is as a result of the spotting of the capture antibodies more towards one edge of the channel walls, resulting in a clipping of their circular shape. The images in FIGS. 18b and 18c clearly demonstrate the successful detection of CRP on our laser-patterned paper-based device with incorporated fluid delay mechanisms. This device is an example of a semi-automatic type test that still requires intervention from a user, but we are planning on developing this concept further in the immediate future to enable a fully-automated device which would then be a true example of a sample-in-result-out type device. In addition, using our devices, we were also able to detect CRP with concentrations of less than ~10 ng/mL, which we believe is close to the limit of detection.

Figure 18:
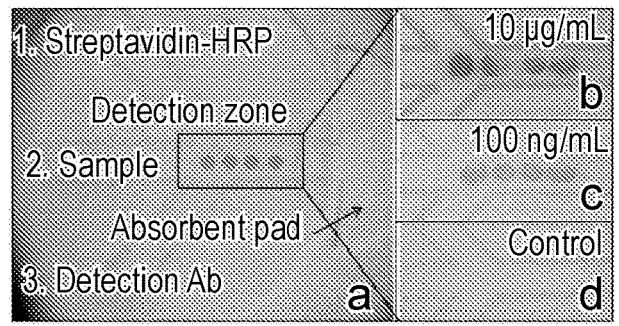
FIG. 18 shows automated multi-step ELISA for CRP detection in a 2D multi-channel fluidic device.

FIG. 18 shows automated multi-step ELISA for CRP detection in a 2D multi-channel fluidic device. a) Image of a device showing its design and indicating reagent locations for the assay. Four blue spots, shown schematically in a), represent the position of immobilized capture antibody in the detection zone. b), c) and d) are photos of the CRP ELISA result on the device for different sample concentrations of 10 µg/mL, 100 ng/mL and no sample respectively.

Conclusions

In this experimental work, we report a new method that allows the fabrication of pre-programmed or timed fluid delivery in paper-based fluidic devices without any additional equipment or minimal actions from the user. Barriers, aligned perpendicular to the flow-path, are used to control the fluid flow in a channel were either impermeable barriers with differing depths, or barriers with differing porosity, and these could be fabricated by simple adjustments of the laser patterning parameters, such as the laser power and the writing speed. Both types of barriers yield similar results for control over the fluid flow. These programmable fluid delay techniques should help to further improve the functionalities of paper-based microfluidic devices as such control can be used to enable (nearly or partially or semi) automated multi-step fluidic protocols. In contrast to other methods reported for controlling fluidic transport, our approach eliminates the requirements for cleanroom-based steps, or custom-designed equipment, or the need for long flow paths, which can then translate into requirements for larger analyte volumes. Most importantly, since the delay-mechanism can be an integral part of the fabrication of the fluidic devices themselves, we believe this integrated process presents a considerable manufacturing and hence commercial advantage. Above all, we believe that this method could be an ideal choice for rapid fabrication of custom-designed paper-based microfluidic devices for realizing single or multistep analytical tests.

REFERENCES

[1] P. Yager, T. Edwards, E. Fu, K. Helton, K. Nelson, M. R. Tam, and B. H. Weigl, "Microfluidic diagnostic technologies for global public health," Nature 442, 412-418 (2006)

[2] X. Li, D. R. Ballerini, and W. Shen, "A perspective on paper-based microfluidics: Current status and future trends," Biomicrofluidics 6, 11301-1130113 (2012)

[3] R. Pelton, "Bioactive paper provides a low-cost platform for diagnostics," Trac-Trends Anal. Chem. 28, 925-942 (2009)

[4] A. K. Yetisen, M. S. Akram, and C. R. Lowe, "Paper-based microfluidic point-of-care diagnostic devices," Lab Chip 13, 2210-2251 (2013)

[5] A. W. Martinez, S. T. Phillips, M. J. Butte, and G. M. Whitesides, "Patterned paper as a platform for inexpensive, low-volume, portable bioassays," Angew. Chem.-Int. Edit. 46, 1318-1320 (2007)

[6] WO 2008/049083

[7] WO 2012/125781

[8] D. A. Bruzewicz, M. Reches, and G. M. Whitesides, "Low-cost printing of poly(dimethylsiloxane) barriers to define microchannels in paper," Anal. Chem. 80, 3387-3392 (2008)

[9] K. Abe, K. Suzuki, and D. Citterio, "Inkjet-printed microfluidic multianalyte chemical sensing paper," Anal. Chem. 80, 6928-6934 (2008)

[10] X. Li, J. F. Tian, T. Nguyen, and W. Shen, "Paper-Based Microfluidic Devices by Plasma Treatment," Anal. Chem. 80, 9131-9134 (2008)

[11] E. M. Fenton, M. R. Mascarenas, G. P. Lopez, and S. S. Sibbett, "Multiplex Lateral-Flow Test Strips Fabricated by Two-Dimensional Shaping," ACS Appl. Mater. Interfaces 1, 124-129 (2009)

[12] Y. Lu, W. W. Shi, L. Jiang, J. H. Qin, and B. C. Lin, "Rapid prototyping of paper-based microfluidics with wax for low-cost, portable bioassay," Electrophoresis 30, 1497-1500 (2009)

[13] l E. Carrilho, A. W. Martinez, and G. M. Whitesides, "Understanding Wax Printing: A Simple Micropatterning Process for Paper-Based Microfluidics," Anal. Chem. 81, 7091-7095 (2009)

[14] X. Li, J. F. Tian, G. Garnier, and W. Shen, "Fabrication of paper-based microfluidic sensors by printing," Colloid Surf. B-Biointerfaces 76, 564-570 (2010)

[15] J. L. Delaney, C. F. Hogan, J. F. Tian, and W. Shen, "Electrogenerated Chemiluminescence Detection in Paper-Based Microfluidic Sensors," Anal. Chem. 83, 1300-1306 (2011)

[16] J. Olkkonen, K. Lehtinen, and T. Erho, "Flexographically Printed Fluidic Structures in Paper," Anal. Chem. 82, 10246-10250 (2010)

[17] W. Dungchai, O. Chailapakul, and C. S. Henry, "A low-cost, simple, and rapid fabrication method for paper-based microfluidics using wax screen-printing," Analyst 136, 77-82 (2011)

[18] G. Chitnis, Z. W. Ding, C. L. Chang, C. A. Savran, and B. Ziaie, "Laser-treated hydrophobic paper: an inexpensive microfluidic platform," Lab Chip 11, 1161-1165 (2011)

[19] C. L. Sones, I. N. Katis, P. J. W. He, B. Mills, M. F. Namiq, P. Shardlow, M. Ibsen and R. W. Eason, "Laser-induced photo-polymerisation for creation of paper-based fluidic devices", Lab Chip 14 (29 Sep. 2014), DOI: 10.1039/C4LC00850B

[20] A. Apilux, et al, Lab Chip 13, 126-135 (2013)
[21] E. Fu et al, Lab Chip 10, 918-920(2010)
[22] B. Lutz et al., Lab Chip 13, 2840-2847 (2013)
[23] GB 1408303.4
[24] GB 1411711.3

The invention claimed is:

1. A method of making a fluid flow device comprising:
providing a substrate of porous material;
depositing a radiation-sensitive substance onto the substrate only in a desired pattern defining one or more regions intended to receive, contain and/or guide fluid during use of the device or occupying an area within such a region, by applying the radiation-sensitive substance locally to the substrate in accordance with the desired pattern, and such that the radiation-sensitive substance extends at least partly through the thickness of the substrate below the pattern; and
applying radiation onto the substrate thereby delivering energy to the radiation-sensitive substance in at least part of the pattern to change the radiation-sensitive substance from a first state to a second state through at least part of the thickness of the substrate, wherein when in one of the first state and the second state, the radiation-sensitive substance is less permeable to the fluid than when in the other of the first state and the second state.

2. A method according to claim 1, wherein in the second state, the radiation-sensitive substance is less permeable to the fluid than in the first state.

3. A method according to claim 1, wherein in said one of the first state and the second state, the radiation-sensitive substance is impermeable to the fluid.

4. A method according to claim 1, wherein in said one of the first state and the second state, the radiation-sensitive substance is partially permeable to the fluid.

5. A method according to claim 1, wherein the radiation-sensitive substance comprises at least one polymerisable material, and said one of the first state and the second state comprises a greater degree of polymerisation state than said other of the first state and the second state.

6. A method according to claim 1, in which for at least one part of the substrate, the radiation-sensitive substance is deposited to extend through the thickness of the substrate, and the radiation-sensitive substance is changed to the second state through the thickness of the substrate.

7. A method according to claim 1, in which for at least one part of the substrate, the radiation-sensitive substance is deposited to extend through substantially the entire thickness of the substrate, and the radiation-sensitive substance is changed to the second state through part of the thickness of the substrate.

8. A method according to claim 1, in which for at least one part of the substrate, the radiation-sensitive substance is deposited to extend through part of the thickness of the substrate, and the radiation-sensitive substance is changed to the second state through said part of the thickness of the substrate.

9. A method according to claim 1, wherein the radiation is applied onto substantially all of the substrate.

10. A method according to claim 1, wherein the radiation is applied onto at least one selected part of the substrate comprising at least part of the pattern.

11. A method according to claim 1, wherein the application of radiation comprises exposing a beam of radiation onto the substrate and causing relative translation between the substrate and the beam of radiation.

12. A method according to claim 11, wherein the pattern comprises lines defining the one or more regions and the method comprises causing relative translation between the substrate and the beam of radiation such that the beam of radiation moves over or along the lines.

13. A method according to claim 12, in which the beam of radiation has a width in a direction parallel to a width of the lines which is at least equal to the width of the lines, and the application of radiation comprises aligning the beam of radiation with the lines to expose substantially all of the width of the lines.

14. A method according to claim 12, in which the application of radiation comprises aligning the beam of radiation with the lines such that the beam of radiation overlaps an edge of at least one line during the relative translation.

15. A method according to claim 14, in which the beam of radiation has a width in a direction parallel to a width of the lines which is equal to or less than the width of the at least one line such that the beam of radiation overlaps only one edge of the at least one line.

16. A method according to claim 14, in which the beam of radiation overlaps an edge which is adjacent to a region intended to receive and contain fluid during use of the device.

17. A method according to claim 12, in which the pattern includes at least one pair of spaced-part lines, the beam of radiation has a width greater than a width of a space between the pair of spaced-apart lines, and the application of radiation comprises aligning the beam of radiation with the pair of spaced-apart lines to simultaneously expose at least part of the width of both lines in the pair of spaced-apart lines.

18. A method according to claim 12, in which the pattern includes at least one pair of spaced-apart lines defining a region in the form of a channel for fluid flow.

19. A method according to claim 12, in which the pattern includes lines defining one or more reservoir or well regions intended to confine received fluid.

20. A method according to claim 11, wherein the application of radiation comprises applying a plurality of sources of radiation onto the substrate.

21. A method according to claim 20, wherein the plurality of sources are applied simultaneously.

22. A method according to claim 20, wherein the plurality of sources are applied sequentially.

23. A method according to claim 1, in which the application of radiation commences before the depositing is complete.

24. A method according to claim 1, in which depositing the radiation-sensitive substance comprises delivering the radiation-sensitive substance onto the substrate using an ink-jet printer.

25. A method according to claim 1, in which the depositing and the application of radiation are performed using an inkjet printer head and a radiation beam delivery system which are carried on a common assembly, the relative translation being between the substrate and the common assembly.

26. A method according to claim 1, in which depositing the radiation-sensitive substance comprises spray printing.

27. A method according to claim 1, in which the radiation comprises a beam of laser light.

28. A method according to claim 1, in which the radiation-sensitive substance is a monomer molecule.

29. A method according to claim 28, in which the radiation-sensitive substance is an ethylenically unsaturated monomer.

30. A method according to claim 1, in which the radiation-sensitive substance comprises a photoresist.

31. A method according to claim 1, in which the porous material is paper, nitrocellulose or a sintered substance.

32. A method according to claim 31, in which the porous material is sintered glass or a sintered polymer.

33. A method according to claim 1, further comprising depositing a biological or chemical reagent onto one or more regions on the substrate.

34. A method according to claim 33, comprising depositing the reagent before the application of radiation.

35. A method according to claim 1, wherein the depositing comprises depositing at least two radiation-sensitive substances onto the substrate in respective patterns.

36. A method according to claim 1, wherein the radiation is applied while some of the radiation-sensitive substance remains on the surface of the substrate.

37. A fluid flow device obtainable using a method according to claim 1.

38. An apparatus configured to make a fluid flow device in accordance with a method according to claim 1.

\* \* \* \* \*